United States Patent
Yamaguchi et al.

(10) Patent No.: US 11,292,979 B2
(45) Date of Patent: Apr. 5, 2022

(54) FLUORINE-CONTAINING ETHER COMPOUND, LUBRICANT FOR MAGNETIC RECORDING MEDIUM AND MAGNETIC RECORDING MEDIUM

(71) Applicant: SHOWA DENKO K.K., Tokyo (JP)

(72) Inventors: Yuta Yamaguchi, Tokyo (JP); Naoya Fukumoto, Tokyo (JP); Naoko Ito, Tokyo (JP); Hiroyuki Tomita, Tokyo (JP); Ichiro Ota, Tokyo (JP); Katsumi Murofushi, Tokyo (JP)

(73) Assignee: SHOWA DENKO K.K., Tokyo (JP)

( * ) Notice: Subject to any disclaimer, the term of this patent is extended or adjusted under 35 U.S.C. 154(b) by 754 days.

(21) Appl. No.: 15/999,837

(22) PCT Filed: Feb. 20, 2017

(86) PCT No.: PCT/JP2017/006182
§ 371 (c)(1),
(2) Date: Aug. 20, 2018

(87) PCT Pub. No.: WO2017/145995
PCT Pub. Date: Aug. 31, 2017

(65) Prior Publication Data
US 2020/0263104 A1 Aug. 20, 2020

(30) Foreign Application Priority Data

Feb. 22, 2016 (JP) .............................. JP2016-031473

(51) Int. Cl.
*C10M 105/54* (2006.01)
*C07C 43/13* (2006.01)
(Continued)

(52) U.S. Cl.
CPC .......... *C10M 105/54* (2013.01); *C07C 43/137* (2013.01); *G11B 5/725* (2013.01); *C10M 2211/0425* (2013.01); *C10N 2040/18* (2013.01)

(58) Field of Classification Search
CPC .......... C10M 105/54; C10M 2211/0425; C07C 43/137; C10N 2040/18; G11B 5/725
See application file for complete search history.

(56) References Cited

U.S. PATENT DOCUMENTS 8,518,564 B2 * 8/2013 Burns ................... G11B 5/725
428/835.8
8,734,966 B2 * 5/2014 Sagata ................... C07C 43/23
428/835.8
(Continued)

FOREIGN PATENT DOCUMENTS

CN 101868521 A 10/2010
CN 102356431 A 2/2012
(Continued)

OTHER PUBLICATIONS

First Office Action dated Nov. 16, 2020, from The China National Intellectual Property Administration in Application No. 201780012549.4.

(Continued)

*Primary Examiner* — James C Goloboy
(74) *Attorney, Agent, or Firm* — Sughrue Mion, PLLC

(57) ABSTRACT

A fluorine-containing ether compound represented by a formula (1) shown below.

$$R^4-CH_2-R^3-CH_2-R^2-CH_2-R^1-CH_2-R^2-CH_2-R^3-CH_2-R^5 \quad (1)$$

In formula (1), $R^1$ and $R^3$ represent the same or different perfluoropolyether chains, $R^2$ represents a linking group containing at least one polar group, one or both of $R^4$ and $R^5$ (Continued)

represent a terminal group containing two or more polar groups, and $R^4$ and $R^5$ are different.

24 Claims, 3 Drawing Sheets

(51) Int. Cl.
    *G11B 5/725*      (2006.01)
    *C10N 40/18*      (2006.01)

(56) References Cited

U.S. PATENT DOCUMENTS

| | | | |
|---|---|---|---|
| 2012/0251873 A1 | 10/2012 | Miyawaki et al. | |
| 2015/0235664 A1 | 8/2015 | Deng et al. | |
| 2017/0337945 A1* | 11/2017 | Nakamura | C10M 111/04 |

FOREIGN PATENT DOCUMENTS

| | | | | |
|---|---|---|---|---|
| EP | 3 225 612 A1 | 10/2017 | | |
| JP | 10-143838 A | 5/1998 | | |
| JP | 2009-211765 A | 9/2009 | | |
| JP | 2010-248463 A | 11/2010 | | |
| JP | 4632144 B2 | 2/2011 | | |
| JP | 2012-007008 A | 1/2012 | | |
| JP | 2012-184339 A | 9/2012 | | |
| JP | 2014-509677 A | 4/2014 | | |
| JP | 5789710 B1 | 10/2015 | | |
| WO | 2012/170009 A2 | 12/2012 | | |
| WO | 2013/054393 A1 | 4/2013 | | |
| WO | 2015/022781 A1 | 2/2015 | | |
| WO | 2016/084781 A1 | 6/2016 | | |
| WO | WO-2016098811 A1 * | 6/2016 | | C10M 105/54 |

OTHER PUBLICATIONS

X.-C. Guo, et al., "A multidentate lubricant for use in hard disk drives at sub-nanometer thickness", Journal of the Applied Physics, 2012, pp. 024503-1-024503-7, vol. 111, No. 2.

International Search Report for PCT/JP2017/006182 dated Apr. 18, 2017 [PCT/ISA/210].

* cited by examiner

FLUORINE-CONTAINING ETHER COMPOUND, LUBRICANT FOR MAGNETIC RECORDING MEDIUM AND MAGNETIC RECORDING MEDIUM

TECHNICAL FIELD

The present invention relates to a magnetic recording medium, a fluorine-containing ether compound, and a lubricant for a magnetic recording medium.

This application is a National Stage of International Application No. PCT/JP2017/006182, filed on Feb. 20, 2017, which claims priority from Japanese Patent Application No. 2016-031473, filed Feb. 22, 2016, the content of which is incorporated herein by reference.

BACKGROUND ART

In order to improve the recording density of magnetic recording and playback devices, the development of magnetic recording media that are suited to high recording densities continues to progress.

Conventional magnetic recording media include media obtained by forming a recording layer on a substrate, and then forming a protective layer of carbon or the like on the recording layer. The protective layer protects the information recorded on the recording layer, and also enhances the slidability of the magnetic head. However, satisfactory durability for the magnetic recording medium cannot be achieved simply by providing a protective layer on the recording layer. As a result, a lubricant layer is generally formed by applying a lubricant to the surface of the protective layer.

Examples of lubricants that have been proposed for the lubricant which is used when forming the lubricant layer for the magnetic recording medium include lubricants containing a fluorine-based polymer having a repeating structure containing $CF_2$ and having polar groups such as hydroxyl groups at the polymer terminals (for example, see Patent Documents 1 to 6).

PRIOR ART LITERATURE

Patent Documents

Patent Document 1: Japanese Unexamined Patent Application, First Publication No. 2010-248463
Patent Document 2: Japanese Unexamined Patent Application, First Publication No. 2012-184339
Patent Document 3: Japanese Unexamined Patent Application, First Publication No. 2012-7008
Patent Document 4: Japanese Patent (Granted) Publication No. 4632144
Patent Document 5: International Patent Publication No. 2013/054393
Patent Document 6: U.S. Patent Application No. 2015/0235664

DISCLOSURE OF INVENTION

Problems to be Solved by the Invention

In magnetic recording and playback devices, further reductions in the floating height of the magnetic head would be desirable. Accordingly, reducing the thickness of the lubricant layer in the magnetic recording medium is desirable.

However, reducing the thickness of the lubricant layer makes the formation of voids in the lubricant layer more likely. As a result, the coverage rate for the lubricant layer coating the surface of the protective layer decreases. If environmental materials that can produce contaminants penetrate through the voids in a lubricant layer having a low coverage rate and reach the underlying layer beneath the lubricant layer, then the environmental materials may produce contaminants such as ionic impurities that can contaminate the magnetic recording medium.

These contaminants (aggregated components) can sometimes adhere (transfer) to the magnetic head as foreign matter (smears) during magnetic recording or playback, which can cause damage to the magnetic head or a deterioration in the magnetic recording and playback characteristics of the magnetic recording and playback device. Further, fluorine-containing ether compounds in the lubricant layer that exist in a state not adhered (adsorbed) to the protective layer can sometimes aggregate and adhere to the magnetic head as foreign matter (smears).

Furthermore, in order to improve the durability of the magnetic recording medium, the lubricant layer must exhibit excellent adhesion to the protective layer.

The present invention has been developed in light of the above circumstances, and has an object of providing a fluorine-containing ether compound that can be used favorably as a material for a magnetic recording medium lubricant that is capable of forming a lubricant layer which, even when having little thickness, can cover the surface of the protective layer with a high coverage rate, has excellent adhesion to the protective layer, and is unlikely to produce foreign matter (smears).

Further, the present invention also has objects of providing a magnetic recording medium lubricant containing the fluorine-containing ether compound of the present invention, and a magnetic recording medium provided with a lubricant layer containing the fluorine-containing ether compound.

Means for Solving the Problems

The inventors of the present invention conducted intensive research aimed at achieving the above objects.

As a result, they discovered that the objects could be achieved by using a fluorine-containing ether compound containing a first perfluoropolyether (hereafter sometimes referred to as "PFPE") chain disposed in the center, a second PFPE chain disposed at each of the two terminals of the first PFPE chain with a linking group containing a polar group disposed therebetween, and mutually different terminal groups disposed at the outside (the opposite side from the first PFPE chain) of the two second PFPE chains, wherein one or both of the terminal groups contain two or more polar groups, and they were therefore able to complete the present invention.

In other words, the present invention relates to the following items.

[1] A fluorine-containing ether compound represented by a formula (1) shown below.

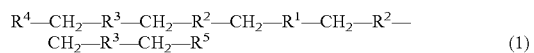

(In formula (1), $R^1$ and $R^3$ represent the same or different perfluoropolyether chains. $R^2$ represents a linking group containing at least one polar group, one or both of $R^4$ and $R^5$ represent a terminal group containing two or more polar groups, and $R^4$ and $R^5$ are different.)

[2] The fluorine-containing ether compound according to [1], wherein $R^4$ and $R^5$ in the formula (1) are each a hydroxyl group, or one terminal group selected from among formulas (2-1) to (2-5) shown below.

[Chemical formula 1]

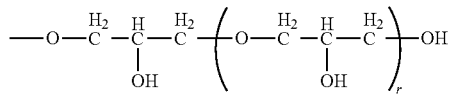

(2-1)

(In formula (2-1), r represents an integer of 0 to 4.)

[Chemical formula 2]

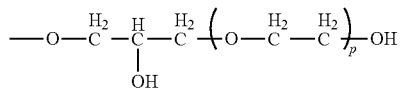

(2-2)

(In formula (2-2), p represents an integer of 1 to 5.)

[Chemical formula 3]

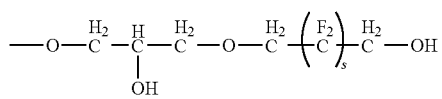

(2-3)

(In formula (2-3), s represents an integer of 2 to 5.)

[Chemical formula 4]

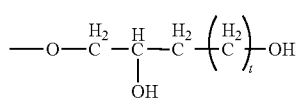

(2-4)

(In formula (2-4), t represents an integer of 1 to 5.)

[Chemical formula 5]

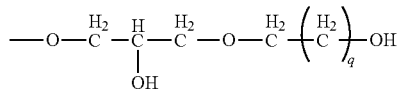

(2-5)

(In formula (2-5), q represents an integer of 2 to 5.)

[3] The fluorine-containing ether compound according to [1] or [2], wherein one or both of $R^1$ and $R^3$ in the formula (1) are represented by a formula (3) shown below.

[Chemical formula 6]

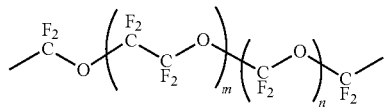

(3)

(In formula (3), m represents an integer of 1 to 20, and n represents an integer of 0 to 10.)

[4] The fluorine-containing ether compound according to [1] or [2], wherein $R^3$ in the formula (1) is represented by a formula (4) shown below or a formula (5) shown below.

[Chemical formula 7]

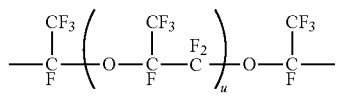

(4)

(In formula (4), u represents an integer of 1 to 30.)

[Chemical formula 8]

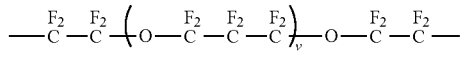

(5)

(In formula (5), v represents an integer of 1 to 30.)

[5] The fluorine-containing ether compound according to any one of [1] to [4], wherein the number of carbon atoms in $R^2$ in the formula (1) is from 1 to 20.

[6] The fluorine-containing ether compound according to any one of [1] to [5], wherein $R^2$ in the formula (1) is represented by a formula (6) shown below.

[Chemical formula 9]

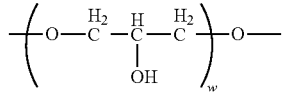

(6)

(In formula (6), w represents an integer of 1 to 4.)

[7] The fluorine-containing ether compound according to any one of [1] to [6], wherein one of $R^1$ and $R^5$ in the formula (1) is a hydroxyl group.

[8] The fluorine-containing ether compound according to any one of [1] to [7], wherein the compound represented by the formula (1) is represented by a formula (D) shown below, and $Rf_1$ in the formula (D) is represented by a formula (RF-1) shown below.

[Chemical formula 10]

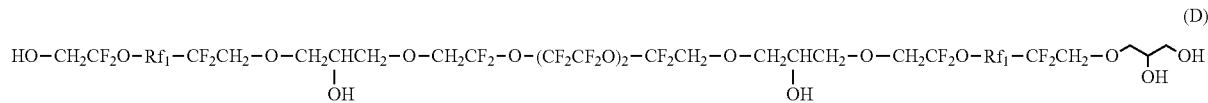
(D)

[Chemical formula 11]

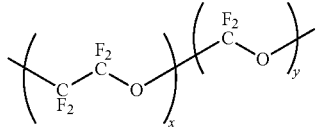
(RF-1)

(In formula (RF-1), x represents an integer of 1 to 7, and y represents an integer of 1 to 7.)

[9] The fluorine-containing ether compound according to any one of [1] to [7], wherein the compound represented by the formula (1) is represented by a formula (G) shown below, and $Rf_1$ in the formula (G) is represented by the formula (RF-1).

[Chemical formula 12]

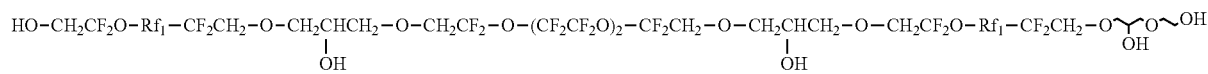
(G)

[10] The fluorine-containing ether compound according to any one of [1] to [7], wherein the compound represented by the formula (1) is represented by a formula (H) shown below, and $Rf_1$ in the formula (H) is represented by the formula (RF-1).

[Chemical formula 13]

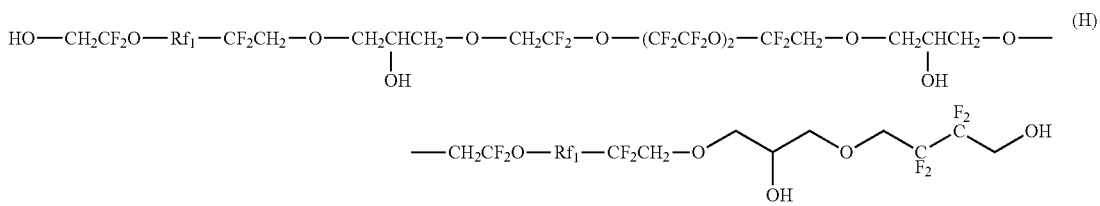
(H)

[11] The fluorine-containing ether compound according to any one of [1] to [7], wherein the compound represented by the formula (1) is represented by a formula (J) shown below, and $Rf_1$ in the formula (J) is represented by the formula (RF-1).

[Chemical formula 14]

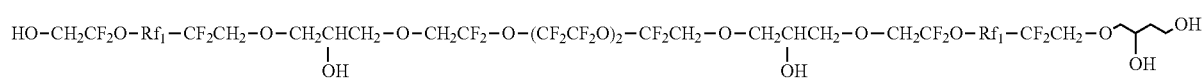
(J)

[12] The fluorine-containing ether compound according to any one of [1] to [7], wherein the compound represented by the formula (1) is represented by a formula (K) shown below, and $Rf_1$ in the formula (K) is represented by the formula (RF-1).

[Chemical formula 15]

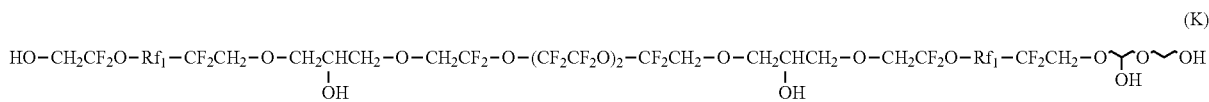
(K)

[13] The fluorine-containing ether compound according to any one of [1] to [7], wherein the compound represented by the formula (1) is represented by a formula (L) shown below, and $Rf_1$ in the formula (L) is represented by the formula (RF-1).

[Chemical formula 16]

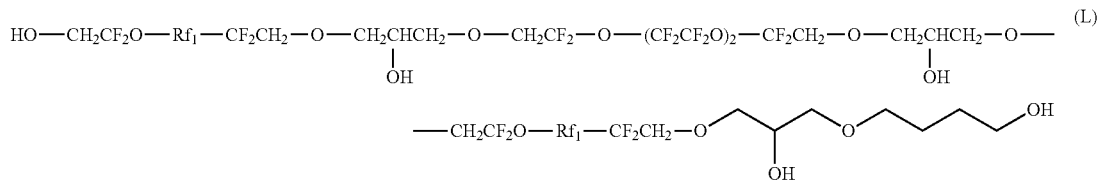
(L)

[14] The fluorine-containing ether compound according to any one of [1] to [7], wherein the compound represented by the formula (1) is represented by a formula (O) shown below, and $Rf_2$ in the formula (O) is represented by a formula (RF-2) shown below.

[Chemical formula 17]

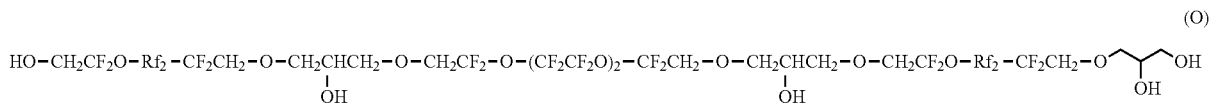
(O)

[Chemical formula 18]

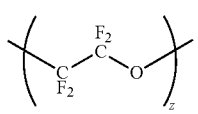
(RF-2)

(In formula (RF-2), z represents an integer of 1 to 9.)

[15] The fluorine-containing ether compound according to any one of [1] to [7], wherein the compound represented by the formula (1) is represented by a formula (Q) shown below, and $Rf_2$ in the formula (Q) is represented by the formula (RF-2).

[Chemical formula 19]

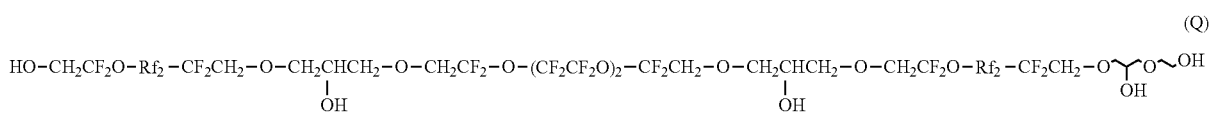
(Q)

[16] The fluorine-containing ether compound according to any one of [1] to [7], wherein the compound represented by the formula (1) is represented by a formula (R) shown below, and $Rf_2$ in the formula (R) is represented by the formula (RF-2).

[Chemical formula 20]

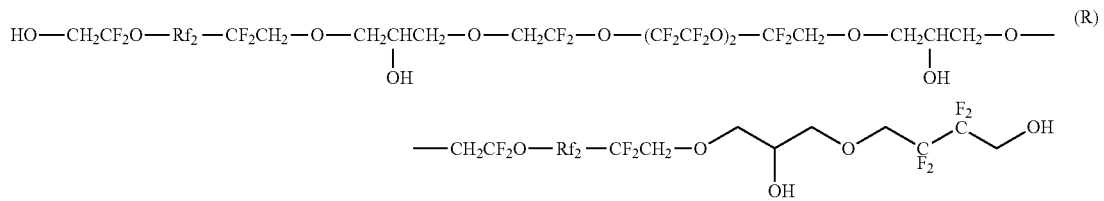

[17] The fluorine-containing ether compound according to any one of [1] to [7], wherein the compound represented by the formula (1) is represented by a formula (U) shown below, and $Rf_1$ in the formula (U) is represented by the formula (RF-1).

[Chemical formula 21]

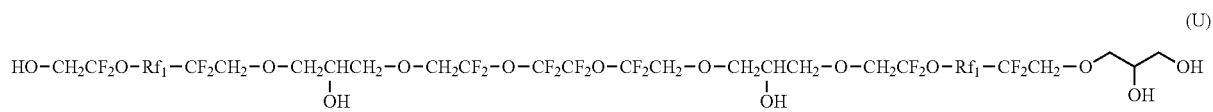

[18] The fluorine-containing ether compound according to any one of [1] to [7], wherein the compound represented by the formula (1) is represented by a formula (X) shown below, and $Rf_1$ in the formula (X) is represented by the formula (RF-1).

[Chemical formula 22]

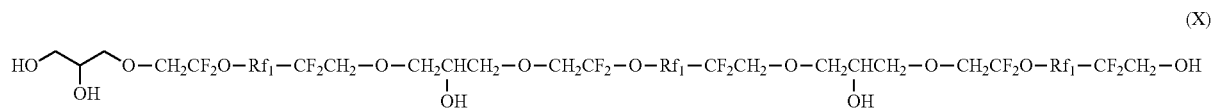

[19] The fluorine-containing ether compound according to any one of [1] to [7], wherein the compound represented by the formula (1) is represented by a formula (Z) shown below, and $Rf_1$ in the formula (Z) is represented by the formula (RF-1).

[Chemical formula 23]

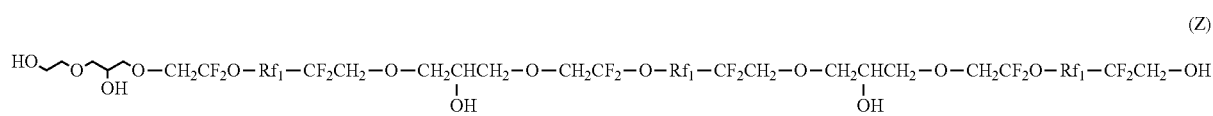

[21] The fluorine-containing ether compound according to any one of [1] to [19], having a number average molecular weight within a range from 1,000 to 10,000.

[21] A lubricant for a magnetic recording medium containing the fluorine-containing ether compound according to any one of [1] to [20].

[22] A magnetic recording medium containing at least a magnetic layer, a protective layer and a lubricant layer provided sequentially on a substrate, wherein the lubricant layer contains the fluorine-containing ether compound according to any one of [1] to [20].

[23] The magnetic recording medium according to [22], wherein an average thickness of the lubricant layer is from 0.5 am to 3 nm.

Effects of the Invention

The fluorine-containing ether compound of the present invention is a compound represented by the above formula (1), and is ideal as the material for a lubricant for a magnetic recording medium.

Because the lubricant for a magnetic recording medium according to the present invention contains the fluorine-containing ether compound of the present invention, even if the thickness of the lubricant layer is reduced, a lubricant layer can be formed that is capable of coating the surface of the protective layer with a high coverage rate, exhibits excellent adhesion to the protective layer, and is unlikely to produce foreign matter (smears).

The magnetic recording medium of the present invention has a lubricant layer that contains the fluorine-containing ether compound of the present invention. As a result, in the magnetic recording medium of the present invention, the surface of the protective layer is coated with the lubricant layer with a high coverage rate, and contamination is suppressed. Because the magnetic recording medium of the present invention has a lubricant layer that exhibits excellent adhesion to the protective layer and is unlikely to produce liquid droplet-type or clay-like foreign matter (smears), the magnetic recording medium exhibits excellent durability.

EMBODIMENTS FOR CARRYING OUT THE INVENTION

Figure 1:
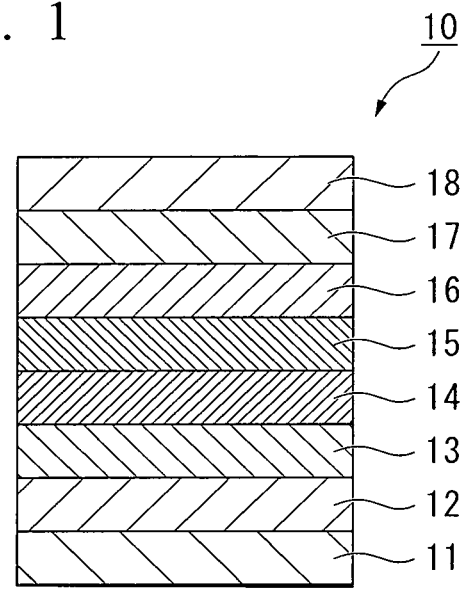
FIG. 1 is a schematic cross-sectional view illustrating one embodiment of the magnetic recording medium of the present invention.

The fluorine-containing ether compound, the lubricant for a magnetic recording medium, and the magnetic recording medium of the present invention are described below in detail. However, the present invention is not limited solely to the embodiments described below.

[Fluorine-Containing Ether Compound]

The fluorine-containing ether compound of the present embodiment is represented by formula (1) shown below.

$$R^4-CH_2-R^3-CH_2-R^2-CH_2-R^1-CH_2-R^2-CH_2-R^3-CH_2-R^5 \quad (1)$$

(In formula (1), $R^1$ and $R^3$ represent the same or different perfluoropolyether chains, $R^2$ represents a linking group containing at least one polar group, one or both of $R^4$ and $R^5$ represent a terminal group containing two or more polar groups, and $R^4$ and $R^5$ are different.)

In those cases where a lubricant for a magnetic recording medium (hereafter also abbreviated as simply "the lubricant") containing the fluorine-containing ether compound of the present embodiment is used to form a lubricant layer on the protective layer of a magnetic recording medium, the reasons why, even if the thickness is reduced, a lubricant layer can be formed that is capable of coating the surface of the protective layer with a high coverage rate, has excellent adhesion to the protective layer, and is unlikely to produce foreign matter (smears) are described below.

As shown in formula (1), the fluorine-containing ether compound of the present embodiment has a first PFPE chain represented by $R^1$, and second PFPE chains represented by $R^3$ that are disposed at the two terminals of the first PFPE chain with linking groups represented by $R^2$ disposed therebetween. In the lubricant layer containing the fluorine-containing ether compound of the present embodiment, the first PFPE chain and the second PFPE chains coat the surface of the protective layer, and reduce frictional force between the magnetic head and the protective layer.

Further, the linking groups represented by $R^2$ in formula (1) contain at least one polar group. One or both of the terminal groups represented by $R^4$ and $R^5$ contain two or more polar groups. In the lubricant layer containing the fluorine-containing ether compound of the present embodiment, the polar groups in the linking groups and the terminal groups bind the fluorine-containing ether compound and the protective layer together.

Specifically, when a lubricant layer is formed on the protective layer using the lubricant containing the fluorine-containing ether compound of the present embodiment, the first PFPE chain is adhered tightly to the protective layer as a result of the bonding between the protective layer and the $R^2$ groups linked to the two ends of the first PFPE chain. Further, either one or both of the two second PFPE chains are adhered tightly to the protective layer as a result of the bonding between the protective layer and the $R^2$ group linked to the first PFPE chain side, and the bonding between the protective layer and the polar groups in the $R^4$ and/or $R^5$ group linked to the outside (the opposite side from the first PFPE chain). Moreover, in the fluorine-containing ether compound of the present embodiment, one or both of $R^4$ and $R^5$ in formula (1) contain two or more polar groups. As a result, the lubricant layer containing the fluorine-containing ether compound of the present embodiment exhibits excellent adhesion to the protective layer, and is bound strongly to the protective layer.

In the lubricant layer described above, as a result of the bonding between the polar groups and the protective layer, the two terminals of the first PFPE chain of the fluorine-containing ether compound, and the two terminals of either one or both of the second PFPE chains are adhered tightly to the protective layer. Consequently, the first PFPE chain and the second PFPE chains are unlikely to aggregate on the protective layer, and the fluorine-containing ether compound in the lubricant layer readily spreads across the protective layer within the in-plane direction and is likely to be arranged in an elongated state. As a result, when using the aforementioned lubricant containing the fluorine-containing ether compound, it is presumed that even if the thickness is reduced, a lubricant layer can be formed that can coat the surface of the protective layer with a high coverage rate.

In addition, in the lubricant layer formed using the lubricant containing the fluorine-containing ether compound of the present embodiment, because $R^4$ and $R^5$ in formula (1) are different, molecules of the fluorine-containing ether compound are less likely to aggregate than compounds in which $R^4$ and $R^5$ are the same. Accordingly, the fluorine-containing ether compound that exists in the lubricant layer without being bound (adsorbed) to the protective layer can be prevented from aggregating and adhering to the magnetic head as foreign matter (smears).

Either one or both of $R^4$ and $R^5$ in formula (1) represent a terminal group containing two or more polar groups, and $R^4$ and $R^5$ are different. A terminal group containing two or more polar groups contributes to the adhesion between the protective layer to which the lubricant containing the fluorine-containing ether compound of the present embodiment is applied, and the lubricant layer formed by applying the lubricant. $R^4$ and $R^5$ in formula (1) may be selected in accordance with the performance and the like required of the lubricant containing the fluorine-containing ether compound. The polar groups in the terminal group containing two or more polar groups represented by $R^4$ or $R^5$ are preferably hydroxyl groups, as hydroxyl groups enable a lubricant layer containing the fluorine-containing ether compound to be obtained that exhibits favorable adhesion to the protective layer.

In those cases where only one of $R^4$ and $R^5$ in formula (1) contains two or more polar groups, the other terminal group is preferably either a terminal group containing one polar group or a terminal group containing no polar groups. Examples of the terminal group containing one polar group include a hydroxyl group, an amino group and an imidazole group.

Examples of the terminal group containing no polar groups include groups in which the active hydrogen atom of a terminal polar group has been substituted, for example, alkylated or esterified hydroxyl groups and functional groups in which an amino group has been subjected to tertiary amination. Specific examples include terminal groups represented by formula (2-0) shown below.

$R^4$ and $R^5$ in formula (1) are each preferably a hydroxyl group, or a terminal group represented by one of formulas (2-1) to (2-5) shown below. These types of $R^4$ and $R^5$ groups contribute to the adhesion between the protective layer to which the lubricant containing the fluorine-containing ether compound of the present embodiment is applied, and the lubricant layer formed by applying the lubricant.

[Chemical formula 24]

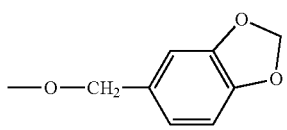
(2-0)

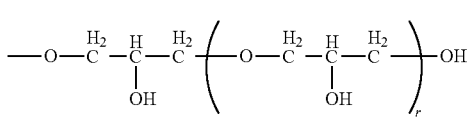
(2-1)

(In formula (2-1), r represents an integer of 0 to 4.)

Formula (2-1) contains two or more hydroxyl groups, and therefore compared with a hydroxyl group, exhibits superior adhesion to the protective layer. In formula (2-1), when r represents an integer of 0 to 4, the number of hydroxyl groups in the fluorine-containing ether compound of the present embodiment is appropriate, and a compound is obtained which can form a lubricant layer that exhibits excellent adhesion to the protective layer and is unlikely to produce foreign matter (smears). Furthermore, r is preferably an integer of 0 to 2, and is most preferably 0.

[Chemical formula 25]

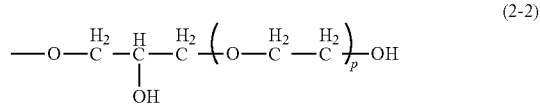
(2-2)

(In formula (2-2), p represents an integer of 1 to 5.)

In formula (2-2), when p represents an integer of 1 to 5, the distance between the $R^3$-side hydroxyl group and the terminal hydroxyl group is appropriate, and a compound is obtained which can form a lubricant layer that exhibits excellent adhesion to the protective layer and is unlikely to produce foreign matter (smears). Furthermore, p is preferably an integer of 1 to 2, and is most preferably 1.

[Chemical formula 26]

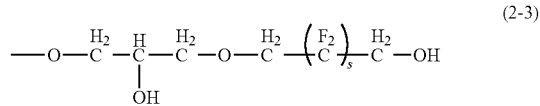
(2-3)

(In formula (2-3), s represents an integer of 2 to 5.)

In formula (2-3), when s represents an integer of 2 to 5, the distance between the $R^3$-side hydroxyl group and the terminal hydroxyl group is appropriate, and a compound is obtained which can form a lubricant layer that exhibits excellent adhesion to the protective layer and is unlikely to produce foreign matter (smears). Furthermore, s is preferably an integer of 2 to 3, and is most preferably 2.

[Chemical formula 27]

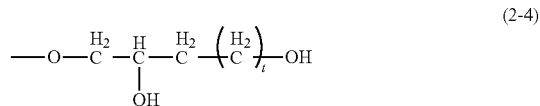
(2-4)

(In formula (2-4), t represents an integer of 1 to 5.)

In formula (2-4), when t represents an integer of 1 to 5, the distance between the $R^3$-side hydroxyl group and the terminal hydroxyl group is appropriate, and a compound is obtained which can form a lubricant layer that exhibits excellent adhesion to the protective layer and is unlikely to produce foreign matter (smears). Furthermore, t is preferably an integer of 1 to 2, and is most preferably 1.

[Chemical formula 28]

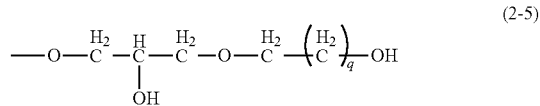
(2-5)

(In formula (2-5), q represents an integer of 2 to 5.)

In formula (2-5), when q represents an integer of 2 to 5, the distance between the $R^3$-side hydroxyl group and the terminal hydroxyl group is appropriate, and a compound is obtained which can form a lubricant layer that exhibits excellent adhesion to the protective layer and is unlikely to produce foreign matter (smears). Furthermore, q is preferably an integer of 2 to 3.

The total number of polar groups in $R^4$ and $R^5$ in formula (1) is two or more, and in terms of obtaining a lubricant layer having excellent adhesion to the protective layer, is preferably 3 or more. The larger the total number of polar groups in $R^4$ and $R^5$ in formula (1), the more likely it becomes that molecules of the fluorine-containing ether compound will undergo aggregation. As a result, the fluorine-containing ether compound in the lubricant layer that exists in a state not adhered (adsorbed) to the protective layer is more likely to aggregate as foreign matter (smears). Accordingly, the total number of polar groups in $R^4$ and $R^5$ in formula (I) is preferably not more than 5, and is more preferably 4 or fewer.

In formula (1), $R^1$ (the first PFPE chain) is a perfluoropolyether chain. When the lubricant containing the fluorine-containing ether compound is applied to the protective layer to form a lubricant layer, the first PFPE chain coats the surface of the protective layer, and imparts the lubricant layer with lubricity that reduces frictional force between the magnetic head and the protective layer.

$R^1$ is not particularly limited, and may be selected appropriately in accordance with the performance and the like required of the lubricant containing the fluorine-containing ether compound.

In formula (I), $R^1$ is preferably a PFPE chain represented by formula (3) shown below, as this facilitates synthesis of the fluorine-containing ether compound.

[Chemical formula 29]

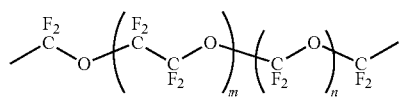

(3)

(In formula (3), m represents an integer of 1 to 20, and n represents an integer of 0 to 10.)

In formula (3), there are no particular limitations on the sequence of the repeating units represented by ($CF_2$—$CF_2$—O) and ($CF_2$—O). In formula (3), the number m of ($CF_2$—$CF_2$—O) units and the number n of ($CF_2$—O) units may be the same or different. The formula (3) may include a random copolymer, a block copolymer or an alternating copolymer composed of the monomer units ($CF_2$—$CF_2$—O) and ($CF_2$—O).

In those cases where $R^1$ is a PFPE chain represented by formula (3), it is more preferable that m in formula (3) is an integer of 1 to 10, and n is an integer of 0 to 10. In such cases, the first PFPE chain is prevented from becoming too long. As a result, when the lubricant layer is formed by applying the lubricant containing the fluorine-containing ether compound to the protective layer, the fluorine-containing ether compound is even less likely to aggregate on the protective layer, and an even thinner lubricant layer can be formed with a satisfactory coverage rate.

Further, m in formula (3) is more preferably an integer of 1 to 7, even more preferably an integer of 1 to 3, even more preferably either 1 or 2, and is most preferably 2. When m in formula (3) is an integer of 1 or more, the first PFPE chain exhibits satisfactory length. As a result, when the lubricant layer is formed on the protective layer using the lubricant containing the fluorine-containing ether compound, the surface of the protective layer is able to be coated with the lubricant layer with a high coverage rate, and good lubricity can be imparted to the lubricant layer.

Moreover, n in formula (3) is more preferably an integer of 1 to 7, and even more preferably an integer of 1 to 5. Further, when n is 0, in is preferably an integer of 1 to 9.

In formula (I), $R^3$ (the second PFPE chains) represents perfluoropolyether chains. In a similar manner to the first PFPE chain, when the lubricant containing the fluorine-containing ether compound is applied to the protective layer to form a lubricant layer, the second PFPE chains coat the surface of the protective layer, and impart the lubricant layer with lubricity that reduces frictional force between the magnetic head and the protective layer.

$R^3$ is not particularly limited, and may be selected appropriately in accordance with the performance and the like required of the lubricant containing the fluorine-containing ether compound. $R^3$ may be the same perfluoropolyether chain as R', or may be a different perfluoropolyether chain. The two $R^3$ chains in formula (1) are the same.

In formula (I), $R^3$ is preferably represented by one of formula (3) shown above, formula (4) shown below and formula (5) shown below. Among these, it is particularly preferable that $R^3$ in formula (1) is represented by formula (3).

When $R^3$ in formula (1) is represented by formula (3), m is preferably an integer of 1 to 20, more preferably an integer of 1 to 10, and even more preferably an integer of 1 to 7. When $R^3$ in formula (1) is represented by formula (3), n is preferably an integer of 0 to 10, and more preferably an integer of 1 to 7. Further, when n is 0, m is preferably an integer of 1 to 9.

[Chemical formula 30]

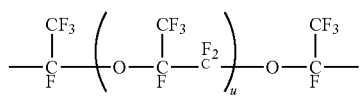

(4)

(In formula (4), u represents an integer of 1 to 30.)

In formula (4), when u represents an integer of 1 to 30, the number average molecular weight of the fluorine-containing ether compound of the present embodiment is more likely to fall within the preferred range. Further, u is more preferably an integer of 3 to 20, and even more preferably an integer of 4 to 10.

[Chemical formula 31]

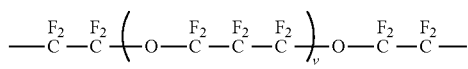

(5)

(In formula (5), v represents an integer of 1 to 30.)

In formula (5), when v represents an integer of 1 to 30, the number average molecular weight of the fluorine-containing ether compound of the present embodiment is more likely to fall within the preferred range. Further, v is more preferably an integer of 3 to 20, and even more preferably an integer of 4 to 10.

In those cases where $R^3$ in formula (I) is represented by one of formula (3) to formula (5), synthesis of the fluorine-containing ether compound is easier, which is desirable. Further, when $R^3$ in formula (1) is represented by one of formula (3) to formula (5), the ratio of the number of oxygen atoms (the number of ether linkages (—O—)) relative to the number of carbon atoms in the perfluoropolyether chain is appropriate. Consequently, a fluorine-containing ether compound having an appropriate level of hardness is obtained. Accordingly, the fluorine-containing ether compound applied to the protective layer is unlikely to undergo aggregation on the protective layer, and an even thinner lubricant layer can be formed with a satisfactory coverage rate. Further, when $R^3$ in formula (1) is represented by formula (3), the number of ether linkages per unit of molecular weight increases, which is particularly preferred in terms of achieving appropriate flexibility.

$R^2$ in formula (I) is a linking group containing at least one polar group. This linking group contributes to the adhesion between the protective layer to which the lubricant containing the fluorine-containing ether compound of the present embodiment is applied, and the lubricant layer formed by applying the lubricant.

The linking group is not particularly limited, and may be selected appropriately in accordance with the performance and the like required of the lubricant containing the fluorine-containing ether compound. Examples of the polar group incorporated in the linking group include a hydroxyl group, carboxyl group, amino group and aminocarboxyl group.

The linking group preferably contains at least one hydroxyl group. If the linking group contains at least one hydroxyl group, then in those cases where the protective layer to which the lubricant is applied is formed from either carbon or carbon which contains nitrogen, the adhesion between the protective layer and the lubricant containing the fluorine-containing ether compound can be improved even further.

There are no particular limitations on the number of polar groups in the linking group, and there may be one polar group or a plurality of polar groups. In order to prevent the number average molecular weight of the fluorine-containing ether compound from becoming too large, the number of polar groups in the linking group is preferably 4 or fewer.

The two $R^2$ groups in formula (1) are the same.

In formula (1), the linking group represented by $R^2$ is preferably a group of 1 to 20 carbon atoms. Provided the number of carbon atoms in the linking group is not more than 20 the number average molecular weight of the fluorine-containing ether compound can be prevented from becoming too large. The number of carbon atoms in the linking group is more preferably from 3 to 12.

In formula (1), $R^2$ is preferably a group represented by formula (6) shown below, as this facilitates synthesis of the fluorine-containing ether compound.

[Chemical formula 32]

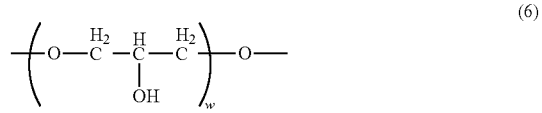

(6)

(In formula (6), w represents an integer of 1 to 4.)

In formula (6), provided w is an integer of 1 or greater, the linking group contains at least one hydroxyl group, meaning the adhesion between the protective layer and the terminal groups improves further, which is desirable. Further, when w is an integer of not more than 4, the number average molecular weight of the fluorine-containing ether compound can be prevented from becoming too large, which is also desirable. Further, w is preferably an integer of 1 or 2, and is most preferably 1.

Specifically, the fluorine-containing ether compound of the present embodiment is preferably a compound represented by one of the formulas (D), (G), (H), (J), (K), (L), (O), (Q), (R), (U), (X) and (Z) shown below. $Rf_1$ in the formulas (D), (G), (H), (J), (K), (L), (U), (X) and (Z) is represented by formula (RF-1) shown below. $Rf_2$ in formulas (O), (Q) and (R) is represented by formula (RF-2) shown below.

[Chemical formula 33]

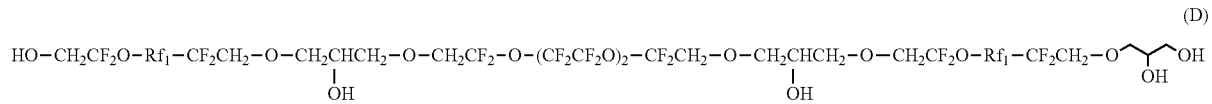

(D)

[Chemical formula 34]

(RF-1)

(In formula (RF-1), x represents an integer of 1 to 7, and y represents an integer of 1 to 7.)
[Chemical formula 35]
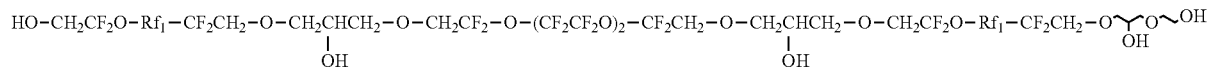
(G)
[Chemical formula 36]
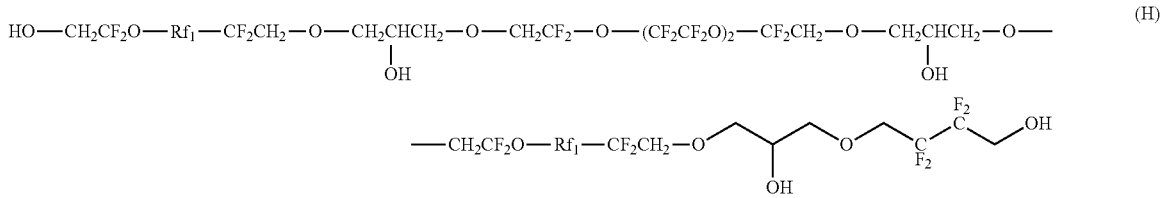
(H)
[Chemical formula 37]
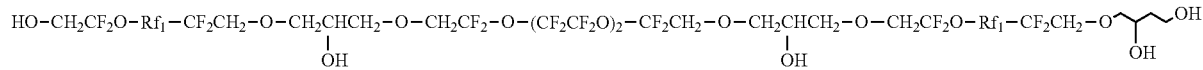
(J)
[Chemical formula 38]
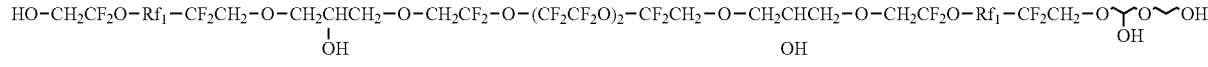
(K)
[Chemical formula 39]
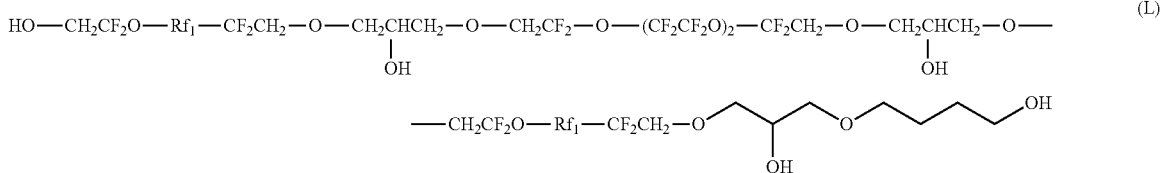
(L)
[Chemical formula 40]
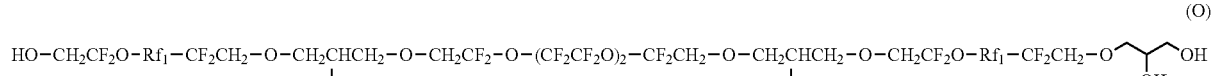
(O)
[Chemical formula 41]
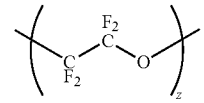
(RF-2)
(In formula (RF-2), z represents an integer of 1 to 9.)
[Chemical formula 42]
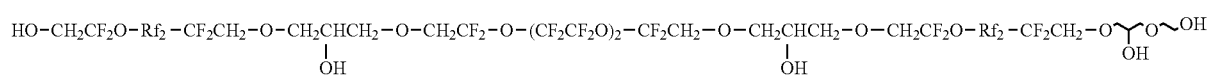
(Q)

[Chemical formula 43]

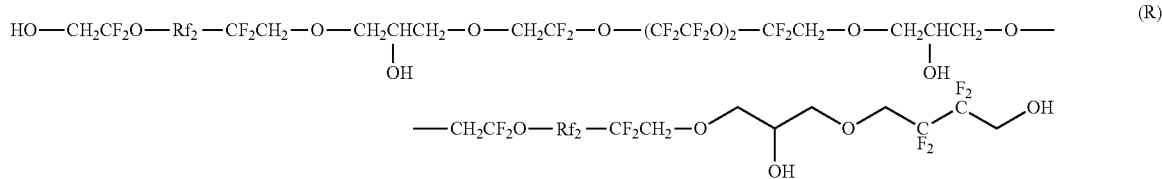
(R)

[Chemical formula 44]

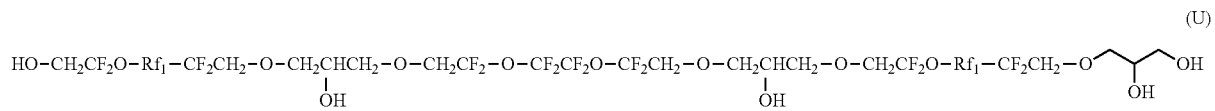
(U)

[Chemical formula 45]

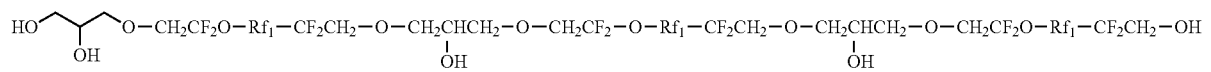
(X)

[Chemical formula 46]

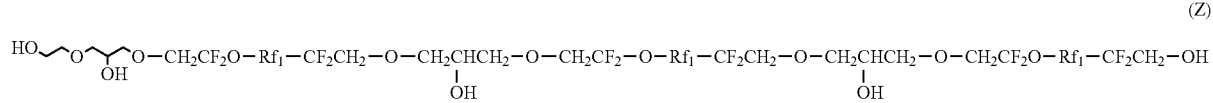
(Z)

Provided the compound represented by formula (1) is a compound represented by one of the above formulas (D), (G), (H), (I), (K), (L), (O), (Q), (R), (U), (X) and (Z), the raw materials are more readily available, which is desirable. Further, compounds represented by one of the above formulas (D), (G), (H), (J), (K), (L), (O), (Q), (R), (U), (X) and (Z) are also preferred in terms of exhibiting excellent coating properties and being resistant to smearing.

The fluorine-containing ether compound of the present embodiment preferably has a number average molecular weight within a range from 7,000 to 10,000. Provided the number average molecular weight is at least 1,000, the lubricant containing the fluorine-containing ether compound of the present embodiment is more resistant to evaporation, meaning evaporation of the lubricant and subsequent adhesion to the magnetic head can be prevented. The number average molecular weight of the fluorine-containing ether compound is more preferably 2,000 or greater. Further, provided the number average molecular weight is not more than 10,000, the viscosity of the fluorine-containing ether compound is appropriate, and a lubricant layer of reduced thickness can be formed easily by application of the lubricant containing the fluorine-containing ether compound. In order to achieve a viscosity that facilitates handling when the fluorine-containing ether compound is used in a lubricant, the number average molecular weight of the fluorine-containing ether compound is preferably 4,000 or less.

The number average molecular weight refers to a value measured by $^{19}$F-NMR using an AVANCE III 400 manufactured by Bruker BioSpin Corporation. In the NMR (nuclear magnetic resonance) measurement, the sample was diluted with a hexafluorobenzene/d-acetone (1/4 v/v) solvent prior to measurement. The standard used for the $^{19}$F-NMR chemical shift was the hexafluorobenzene peak at −164.7 ppm, whereas the standard used for the $^1$H-NMR chemical shift was the acetone peak at 2.2 ppm.

[Production Method]

There are no particular limitations on the method used for producing the fluorine-containing ether compound of the present embodiment, and conventional production methods may be used. For example, the production method described below may be used.

First, an epoxy compound having terminal epoxy groups corresponding with the —$CH_2$—$R^2$— groups at both terminals of $R^1$ in formula (1) is synthesized. Next, the synthesized epoxy compound and a compound having —$CH_2OH$ groups at both terminals and having a perfluoropolyether chain corresponding with $R^3$ in formula (1) are reacted via a ring-opening addition reaction of the epoxy groups in the epoxy compound. This method yields a compound in which both terminals in formula (1) are hydroxyl groups (HO—$CH_2$—$R^3$—$CH_2$—$R^2$—O—$CH_2$—$R^1$—$CH_2$—$R^2$—$CH_2$—$R^3$—$CH_2$—OH).

Subsequently, for example, by reacting the thus obtained compound with glycidol, a mixture is produced containing a compound in which one of $R^4$ and $R^5$ is a terminal group represented by formula (2-1) and the other is a hydroxyl group, and a compound in which both terminals are terminal groups represented by formula (2-1). The compound in which one of $R^4$ and $R^5$ is a terminal group represented by formula (2-1) and the other is a hydroxyl group, and the compound in which both terminals are terminal groups represented by formula (2-1) can be separated, for example, using a method such as column chromatography.

Further, for example, the compound (HO—$CH_2$—$R^3$—$CH_2$—$R^2$—$CH_2$—$R^1$—$CH_2$—$R^2$—$CH_2$—$R^3$—$CH_2$—OH) may be used to synthesize an epoxy compound having an epoxy group at one terminal, which is then reacted with a compound selected from among ethylene glycol, 2,2,3,3-fluorobutane-1,4-diol, propanediol and butanediol. By using this method, a compound can be produced in which one of $R^4$ and $R^5$ is a terminal group represented by one of formulas (2-2), (2-3) and (2-5), and the other is a hydroxyl group.

Furthermore, for example, the compound (HO—$CH_2$—$R^3$—$CH_2$—$R^2$—$CH_2$—$R^1$—$CH_2$—$R^2$—$CH_2$—$R^3$—

CH$_2$—OH) may be reacted with an epoxy compound (I) shown below that can be synthesized from 3-butanyl acetate. By using this method, a compound can be produced in which one of R$^4$ and R$^5$ is a terminal group represented by formula (2-4), and the other is a hydroxyl group.

The fluorine-containing ether compound of the present embodiment is a compound represented by the formula (1) shown above. Accordingly, when a lubricant layer is formed on a protective layer using a lubricant containing this compound, the surface of the protective layer is coated with the first PFPE chain represented by R$^1$ in formula (1) and the second PFPE chains represented by R$^3$, and frictional force between the magnetic head and the protective layer is reduced.

Further, as a result of the bonding between the protective layer and the polar groups in the linking groups represented by R$^2$ that are linked to the two terminals of the first PFPE chain, the first PFPE chain is adhered tightly to the protective layer. Further, as a result of the bonding between the protective layer and the polar groups in the R$^2$ groups linked to the first PFPE chain-side of the second PFPE chains, and the bonding between the protective layer and the polar groups in R$^4$ and/or R$^5$ linked to the outsides of the second PFPE chains, either one or both of the two second PFPE chains are adhered tightly to the protective layer. As a result, the lubricant layer and the protective layer are bound together strongly.

Further, in the lubricant layer described above, as a result of the bonding between the polar groups and the protective layer, both terminals of the first PFPE chain in the fluorine-containing ether compound and both terminals of either one or both of the second PFPE chains are adhered tightly to the protective layer. As a result, the first PFPE chain and the second PFPE chains are unlikely to aggregate on the protective layer, and the fluorine-containing ether compound in the lubricant layer readily spreads across the protective layer within the in-plane direction and is likely to be arranged in an elongated state. As a result, when using the lubricant containing the fluorine-containing ether compound, it is presumed that even if the thickness is reduced, a lubricant layer can be formed that can coat the surface of the protective layer with a high coverage rate.

In addition, in the lubricant layer formed using the lubricant containing the fluorine-containing ether compound of the present embodiment, because R$^4$ and R$^5$ in formula (1) are different, molecules of the fluorine-containing ether compound are less likely to aggregate than compounds in which R$^4$ and R$^5$ are the same. Accordingly, the fluorine-containing ether compound that exists in the lubricant layer without being bound (adsorbed) to the protective layer can be prevented from aggregating and adhering to the magnetic head as foreign matter (smears).

Further, by forming a lubricant layer on the protective layer using a lubricant containing the fluorine-containing ether compound described above, environmental materials that penetrate through to the lower layer of the lubricant layer can be prevented from producing liquid droplet-type or clay-like foreign matter (smears) which can contaminate the magnetic recording medium.

In contrast, in those cases where, for example, a compound having hydroxyl groups at both terminals of the perfluoropolyether chain is used as the fluorine-containing ether compound, if the thickness of the lubricant layer formed on the protective layer is reduced, then a satisfactory coverage rate cannot be obtained. It is thought that this is because the lack of linking groups means that the fluorine-containing ether compound is more likely to aggregate on the protective layer in the thickness direction of the protective layer, and is less likely to spread evenly across the protective layer in the in-plane direction. Further, because of the lack of linking groups, the adhesion to the protective layer also tends to be unsatisfactory, and therefore making the lubricant layer thinner is problematic.

[Lubricant for Magnetic Recording Medium]

A lubricant for a magnetic recording medium according to this embodiment contains the fluorine-containing ether compound represented by formula (1).

In the lubricant of the present embodiment, conventional materials typically used as lubricant materials may be added and mixed as required, provided that the properties of the fluorine-containing ether compound represented by formula (1) are not impaired.

Examples of these conventional materials include Fomblin (a registered trademark) ZDIAC, Fomblin ZDEAL and Fomblin AM-2001 (all manufactured by Solvay Solexis S.A.), and Moresco A20H (manufactured by Moresco Corporation). Conventional materials that are mixed and used with the lubricant of the present embodiment preferably have a number average molecular weight of 1,000 to 10,000.

In those cases where the lubricant of the present embodiment contains materials other than the fluorine-containing ether compound represented by formula (1), the amount of the fluorine-containing ether compound represented by formula (1) within the lubricant of the present embodiment is preferably at least 50% by mass, and more preferably 70% by mass or greater.

Because the lubricant of the present embodiment contains the fluorine-containing ether compound represented by formula (1), even if the thickness is reduced, a lubricant layer can be formed that can coat the surface of the protective layer with a high coverage rate and also exhibits excellent adhesion to the protective layer. Accordingly, contamination of the magnetic recording medium can be suppressed. As a result, by using the lubricant of the present embodiment, a magnetic recording medium can be provided that has little contamination such as foreign matter (smears) on the surface. Moreover, because the lubricant of the present embodiment contains the fluorine-containing ether compound represented by formula (1), any fluorine-containing ether compound that exists in the lubricant layer without being bound (adsorbed) to the protective layer is unlikely to undergo aggregation. Accordingly, the problem of the fluorine-containing ether compound aggregating and adhering to the magnetic head as foreign matter (smears) can be prevented.

[Magnetic Recording Medium]

FIG. 1 is a schematic cross-sectional view illustrating one embodiment of the magnetic recording medium of the present invention.

The magnetic recording medium 10 of this embodiment has a structure in which an adhesive layer 12, a soft magnetic layer 13, a first base layer 14, a second base layer 15, a magnetic layer 16, a protective layer 17, and a lubricant layer 18 are provided in sequence on a substrate 11.

[Substrate]

Examples of materials that can be used as the substrate 11 include non-magnetic substrates having a film composed of NiP or a NiP alloy formed on a substrate formed from a metal or an alloy material such as Al or an Al alloy.

Further, non-magnetic substrates formed from non-metal materials such as glass, ceramic, silicon, silicon carbide, carbon or resin may be used as the substrate 11, and non-magnetic substrates having a film composed of NiP or a NiP alloy formed on a substrate formed from one of these non-metal materials may also be used.

[Adhesive Layer]

The adhesive layer 12, when disposed so as to contact the substrate 11 and the soft magnetic layer 13 provided on top of the adhesive layer 12, prevents any progression of corrosion of the substrate 11.

The material for the adhesive layer 12 may be selected appropriately, for example, from among Cr, Cr alloys, Ti, and Ti alloys and the like. The adhesive layer 12 can be formed, for example, by a sputtering method.

[Soft Magnetic Layer]

The soft magnetic layer 13 preferably has a structure in which a first soft magnetic film, an intermediate layer formed from a Ru film, and a second soft magnetic film are stacked sequentially. In other words, the soft magnetic layer 13 preferably has a structure in which, by sandwiching an intermediate layer formed from a Ru film between two layers of soft magnetic film, the soft magnetic films above and below the intermediate layer are linked by antiferromagnetic coupling (AFC). When the soft magnetic layer 13 has an AFC coupled structure, the resistance to externally applied magnetic fields, and the durability relative to the WATE (Wide Area Track Erasure) phenomenon, which is a problem peculiar to perpendicular magnetic recording, can both be enhanced.

The first soft magnetic film and the second soft magnetic film are preferably films formed from a CoFe alloy. When the first soft magnetic film and the second soft magnetic film are films formed from a CoFe alloy, a high saturation magnetic flux density Bs (of at least 1.4 (T)) can be achieved.

Further, one of Zr, Ta and Nb is preferably added to the CoFe alloy used in forming the first soft magnetic film and the second soft magnetic film. This promotes the amorphization of the first soft magnetic film and the second soft magnetic film, which enables the orientation of the first base layer (seed layer) to be improved, and also enables a reduction in the floating height of the magnetic head.

The soft magnetic layer 13 can be formed, for example, by a sputtering method.

[First Base Layer]

The first base layer 14 is a layer for controlling the orientation and crystal size of the second base layer 15 and the magnetic layer 16 provided on top of the first base layer 14. The first base layer 14 is provided to increase the perpendicular direction component of the flux generated by the magnetic head that is perpendicular to the substrate surface, and also to fix the direction of magnetization of the magnetic layer 16 more strongly in a direction perpendicular to the substrate 11.

The first base layer 14 is preferably a layer formed from a NiW alloy. When the first base layer 14 is a layer formed from a NiW alloy, other elements such as B, Mn, Ru, Pt, Mo and Ta may be added to the NiW as required.

The first base layer 14 can be formed, for example, by a sputtering method.

[Second Base Layer]

The second base layer 15 is a layer that controls the orientation of the magnetic layer 16 to achieve a more favorable orientation. The second base layer 15 is preferably a layer formed from Ru or a Ru alloy.

The second base layer 15 may be composed of a single layer, or may be composed of a plurality of layers. When the second base layer 15 is composed of a plurality of layers, all of the layers may be formed from the same material, or at least one layer may be formed from a different material.

The second base layer 15 can be formed, for example, by a sputtering method.

[Magnetic Layer]

The magnetic layer 16 is formed from a magnetic film having an easy axis of magnetization that is oriented in either the perpendicular direction or the horizontal direction relative to the substrate surface. The magnetic layer 16 is a layer containing Co and Pt, and may also contain oxides, or Cr, B, Cu, Ta or Zr or the like, in order to improve the SNR characteristics.

Examples of oxides that may be included in the magnetic layer 16 include $SiO_2$, SiO, $Cr_2O_3$, CoO, $Ta_2O_3$ and $TiO_2$.

The magnetic layer 16 may be composed of a single layer, or may be composed of a plurality of magnetic layers formed from materials having different compositions.

For example, in the case where the magnetic layer 16 is composed of three layers, namely a first magnetic layer, a second magnetic layer and a third magnetic layer, the first magnetic layer preferably has a granular structure formed from a material containing Co, Cr and Pt, and also containing oxides. Examples of preferred oxides that may be used for inclusion in the first magnetic layer include oxides of Cr, Si, Ta, Al, Ti, Mg and Co. Among these, oxides such as $TiO_2$, $Cr_2O_3$ and $SiO_2$ can be used particularly favorably. Further the first magnetic layer is preferably formed from a composite oxide containing two or more added oxides. Among such composite oxides, $Cr_2O_3$—$SiO_2$, $Cr_2O_3$—TiO, and $SiO_2$—$TiO_2$ and the like can be used particularly favorably.

The first magnetic layer may also contain, in addition to Co, Cr, Pt and the oxides, one or more elements selected from among B, Ta, Mo, Cu, Nd, W, Nb, Sm, Tb, Ru and Re. By including one or more of the above elements, micronization of the magnetic particles can be promoted, and the crystallinity and orientation can be improved, meaning recording and playback characteristics and thermal fluctuation characteristics suitable for higher density recording can be obtained.

The same materials as those used for the first magnetic layer can be used for the second magnetic layer. The second magnetic layer preferably has a granular structure.

The third magnetic layer preferably has a non-granular structure formed from a material containing Co, Cr and Pt, but containing no oxides. In addition to Co, Cr and Pt, the third magnetic layer may also contain one or more elements selected from among B, Ta, Mo, Cu, Nd, W, Nb, Sm, Tb, Ru, Re and Mn. By including one or more of the above elements in the third magnetic layer in addition to Co, Cr and Pt, micronization of the magnetic particles can be promoted, and the crystallinity and orientation can be improved, meaning recording and playback characteristics and thermal fluctuation characteristics suitable for higher density recording can be obtained.

In those cases where the magnetic layer 16 is composed of a plurality of magnetic layers, a non-magnetic layer is preferably provided between adjacent magnetic layers. When the magnetic layer 16 is composed of three layers, namely a first magnetic layer, a second magnetic layer and a third magnetic layer, a non-magnetic layer is preferably provided between the first magnetic layer and the second magnetic layer, and between the second magnetic layer and the third magnetic layer.

By providing a non-magnetic layer of an appropriate thickness between adjacent magnetic layers, magnetization reversal of each of the layers is easier, and the variance in the magnetization reversal over all the magnetic particles can be reduced, enabling the S/N ratio to be improved.

Examples of materials that can be used favorably for the non-magnetic layers provided between the adjacent magnetic layers of the magnetic layer 16 include Ru, Ru alloys, CoCr alloys, and CoCrX1 alloys (wherein X1 represents one or more elements selected from among Pt, Ta, Zr, Re, Ru, Cu, Nb, Ni, Mn, Ge, Si, O, N, W, Mo. Ti, V, Zr and B) and the like.

Alloy materials containing oxides, metal nitrides or metal carbides are preferably used for the non-magnetic layers provided between the adjacent magnetic layers of the magnetic layer 16. Specific examples of oxides that may be used include $SiO_2$, $Al_2O_3$, $Ta_2O_5$, $Cr_2O_3$, MgO, $Y_2O_3$ and $TiO_2$. Examples of metal nitrides that may be used include AlN, $Si_3N_4$, TaN and CrN. Examples of metal carbides that may be used include TaC, BC and SiC.

The non-magnetic layers may be formed, for example, by a sputtering method.

In order to achieve a higher recording density, the magnetic layer 16 is preferably a magnetic layer for perpendicular magnetic recording, in which the easy axis of magnetization is oriented in a direction perpendicular to the substrate surface, but in-plane magnetic recording, layers may also be used.

The magnetic layer 16 may be formed using any conventional method such as a vapor deposition method, ion beam sputtering method or magnetron sputtering method, but is usually formed by a sputtering method.

[Protective Layer]

The protective layer 17 is a layer for protecting the magnetic layer 16. The protective layer 17 may be composed of a single layer, or may be composed of a plurality of layers. Examples of the material for the protective layer 17 include carbon, carbon which contains nitrogen, and silicon carbide.

Examples of the method used for depositing the protective layer 17 include deposition) methods using a hydrocarbon raw material such as ethylene or toluene, and IBD (ion beam deposition) methods.

[Lubricant Layer]

The lubricant layer 18 prevents contamination of the magnetic recording medium 10. Further, the lubricant layer 18 also reduces the frictional force of the magnetic head of the magnetic recording and playback device that slides across the top of the magnetic recording medium 10, and improves the durability of the magnetic recording medium 10.

As illustrated in FIG. 1, the lubricant layer 18 is formed so as to contact the protective layer 17. The lubricant layer 18 is formed by applying the magnetic recording medium lubricant of the embodiment described above to the protective layer 17. Accordingly, the lubricant layer 18 contains the fluorine-containing ether compound described above.

In those cases where the protective layer 17 disposed beneath the lubricant layer 18 is formed from carbon, carbon which contains nitrogen, or silicon carbide, the lubricant layer 18 bonds to the fluorine-containing ether compound contained in the protective layer 17 with powerful bonding strength. As a result, even if the thickness of the lubricant layer 18 is reduced, a magnetic recording medium 10 in which the surface of the protective layer 17 is coated with a high coverage rate can be obtained easily, and contamination of the surface of the magnetic recording medium 10 can be effectively prevented.

The average thickness of the lubricant layer 18 is preferably from 0.5 nm (5 Å) to 3 nm (30 Å), and is more preferably from 0.5 nm (5 Å) to 2 nm (20 Å).

Provided the average thickness of the lubricant layer 18 is at least 0.5 nm, the lubricant layer 18 is formed with uniform thickness without becoming an island-like or network-like layer. As a result, the surface of the protective layer 17 can be coated with the lubricant layer 18 with a high coverage rate. Further, by ensuring that the average thickness of the lubricant layer 18 is not more than 3 nm, the floating height of the magnetic head can be satisfactorily reduced, and the recording density of the magnetic recording medium 10 can be increased.

When the surface of the protective layer 17 is not coated with the lubricant layer 18 with a satisfactorily high coverage rate, environmental materials adsorbed to the surface of the magnetic recording medium 10 can pass through voids in the lubricant layer 18 and penetrate beneath the lubricant layer 18. Environmental materials that penetrate beneath the lubricant layer 18 can adsorb and bond to the protective layer 17, producing contaminants. Then, during magnetic recording or playback, these contaminants (aggregated components) can adhere (transfer) to the magnetic head as smears, and cause damage to the magnetic head, or cause a deterioration in the magnetic recording and playback characteristics of the magnetic recording and playback device.

Examples of the environmental materials that can produce contaminants include siloxane compounds (cyclic siloxanes and linear siloxanes), ionic compounds, comparatively high-molecular weight hydrocarbons such as octacosane, and plasticizers such as dioctyl phthalate. Examples of metal ions contained in ionic impurities include sodium ions and potassium ions and the like. Examples of inorganic ions contained in ionic impurities include chloride ions, bromide ions, nitrate ions, sulfate ions and ammonium ions. Examples of organic ions contained in ionic impurities include oxalate ions and formate ions.

[Lubricant Layer Formation Method]

One example of the method used for forming the lubricant layer 18 is a method in which a partially produced magnetic recording medium is first prepared having each of the layers up to and including the protective layer 17 formed on the substrate 11, and a solution for forming the lubricant layer is then applied to the protective layer 17.

The solution for forming the lubricant layer is obtained by diluting the magnetic recording medium lubricant of the embodiment described above with a solvent as necessary, so as to achieve a viscosity and concentration that are suitable for the coating method.

Examples of the solvent used in the solution for forming the lubricant layer include fluorine-based solvents such as Vertrel (a registered trademark) XF (a product name, manufactured by Mitsui DuPont Fluorochemicals Co., Ltd.) and the like.

There are no particular limitations on the coating method used for applying the solution for forming the lubricant layer, and examples include spin-coating methods and dipping methods.

When a dipping method is used, for example, the method described below may be used. First, the substrate 11 having the various layer up to and including the protective layer 17 is dipped in the solution for forming the lubricant layer which is placed in the dipping tank of a clip coating device. Subsequently, the substrate 11 is pulled up out of the dipping tank at a prescribed speed. This coats the solution for forming the lubricant layer onto the protective layer 17 of the substrate 11.

By using a dipping method, the solution for forming the lubricant layer can be applied uniformly to the surface of the protective layer 17, enabling the lubricant layer 18 to be formed with uniform thickness on the protective layer 17.

The magnetic recording medium 10 of the present embodiment has at least the magnetic layer 16, the protective layer 17 and the lubricant layer 18 provided sequentially on the substrate 11. In the magnetic recording medium 10 of the present embodiment, the lubricant layer 18 containing the fluorine-containing ether compound described above is formed so as to contact the protective layer 17. Even if the thickness of this lubricant layer 18 is reduced, the surface of the protective layer 17 can be coated with a high coverage rate. Accordingly, in the magnetic recording medium 10 of the present embodiment, the problem of environmental materials that can produce contaminants such as ionic impurities penetrating through voids in the lubricant layer 18 can be prevented. Accordingly, the magnetic recording medium 10 of the present embodiment is a medium in which few contaminants exist on the surface. Further, the lubricant layer 18 in the magnetic recording medium 10 of the present embodiment is unlikely to produce foreign matter (smears).

EXAMPLES

The present invention is described below in further detail using examples and comparative examples. However, the present invention is not limited solely to the following examples.

Example 1

A 500 mL round bottom flask was charged with 1H,1H,11H,11H-dodecafluoro-3,6,9-trioxaundecane-1,11-diol (10 g), acetone (150 mL), and 7.8 g of an aqueous solution of sodium hydroxide (NaOH/water=3.9 g/3.9 g) to produce a mixture. The thus obtained mixture was heated, and stirred under reflux at 75° C. for one hour.

Next, epibromohydrin (28 mL) was added to the above mixture, and the resulting mixture was stirred under reflux at 75° C. for 5 hours, and was then cooled to 25° C. Subsequently, ethyl acetate was added to the round bottom flask, the flask contents were washed with water, and the organic phase inside the round bottom flask was collected. Sodium sulfate was then added to the collected organic phase to perform dewatering, and the mixture was then filtered through a filter. Subsequently, an evaporator was used to remove the solvent from the filtrate by distillation. A distillation under reduced pressure (130° C., 6.7×10$^{-5}$ MPa) was then performed to obtain a colorless and transparent liquid compound 1a (18 g) represented by a formula (A) shown below.

$^1$H-NMR and $^{19}$F-NMR measurements of the obtained compound 1a were performed, and the structure was identified based on the following results.

(Identification Data)

$^1$H-NMR (acetone-D$_6$): δ [ppm]=2.60 (2H), 2.77 (2H), 3.15 (2H), 3.56 (2H), 4.04 (6H)

$^{19}$F-NMR (acetone-D$_6$): δ [ppm]=−89.63 to −89.35 (4F), −89.27 to −89.13 (4F), −79.04 to −78.73 (4F)

[Chemical formula 47]

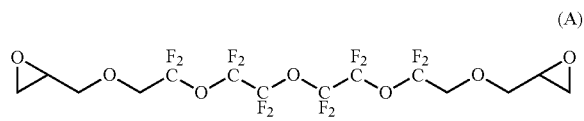

(A)

Next, a 100 mL round bottom flask was charged, under a nitrogen atmosphere, with the compound 1a represented by formula (A) (1 g) and a fluoropolyether represented by HOCH$_2$CF$_2$O(CF$_2$CF$_2$O)$_x$(CF$_2$O)$_y$CF$_2$CH$_2$OH (wherein x=1 to 7, y=1 to 7, number average molecular weight: 800, molecular weight distribution: 1.1) (28 g), and stirring was performed until a uniform mixture was obtained. Subsequently, 0.8 g of potassium carbonate was added to the mixture, and the mixture was stirred for 15 hours while heating at 70° C., and was then cooled to 25° C.

Subsequently, a neutralization was performed by adding hydrochloric acid to the round bottom flask, a fluorine-based solvent (product name: ASAHIKLIN (a registered trademark) AK-225, manufactured by Asahi Glass Co., Ltd.) was added, the flask contents were washed with water, and the organic phase inside the round bottom flask was collected. Sodium sulfate was then added to the collected organic phase to perform dewatering, and the mixture was then filtered through a filter. Subsequently, an evaporator was used to remove the solvent from the filtrate by distillation. A supercritical extraction was then performed under conditions of 60° C. and 14 MPa to obtain a colorless and transparent liquid compound 2a (3 g) represented by a formula (B) shown below. Rf$_1$ in the following formula (B) is represented by formula (RF-1) shown below.

$^1$H-NMR and $^{19}$F-NMR measurements of the obtained compound 2a were performed, and the structure was identified based on the following results.

(Identification Data)

$^1$H-NMR (acetone-D$_6$): δ [ppm]=3.74 to 3.81 (4H), 3.81 to 4.02 (10H), 4.04 to 4.16 (8H)

$^{19}$F-NMR (acetone-D$_6$): δ [ppm]=−91.15 to −88.51 (36F), −83.19 (2F), −81.23 (2F), −80.61 (2F), −78.81 to −78.45 (6F), −55.65 to −51.59 (12F)

[Chemical formula 48]

(B)

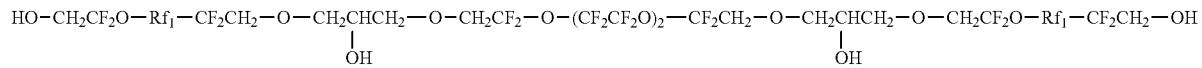

HO—CH$_2$CF$_2$O—Rf$_1$—CF$_2$CH$_2$—O—CH$_2$CHCH$_2$—O—CH$_2$CF$_2$—O—(CF$_2$CF$_2$O)$_2$—CF$_2$CH$_2$—O—CH$_2$CHCH$_2$—O—CH$_2$CF$_2$O—Rf$_1$—CF$_2$CH$_2$—OH
                                                          |                                                              |
                                                         OH                                                            OH

[Chemical formula 49]

(RF-1)

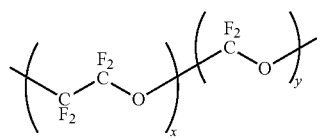

(In formula (RF-1), x represents an integer of 1 to 7, and y represents an integer of 1 to 7.)

Next, a 300 mL round bottom flask was charged, under a nitrogen atmosphere, with the compound 2a represented by formula (B) (4 g) and t-butanol (40 mL), and stirring was performed until a uniform mixture was obtained. Subsequently, potassium tert-butoxide (0.1 g) was added to the mixture, and with the mixture undergoing stirring at 70° C., glycidol (250 μL) was added, and the resulting mixture was then stirred for 8 hours, and then cooled to 25° C.

Subsequently, a neutralization was performed by addling hydrochloric acid to the round bottom flask, a fluorine-based solvent (product name: ASAHIKLIN (a registered trademark) AK-225, manufactured by Asahi Glass Co., Ltd.) was added, the flask contents were washed with water, and the organic phase inside the round bottom flask was collected. Sodium sulfate was then added to the collected organic phase to perform dewatering, and the mixture was then filtered through a filter. Subsequently, an evaporator was used to remove the solvent from the filtrate by distillation. The resulting residue was separated by column chromatography. The above steps yielded a colorless and transparent liquid compound D: 3a (1.8 g) represented by a formula (D) shown below. $Rf_1$ in the following formula (D) is represented by the formula (RF-1) shown above.

Figure 3:
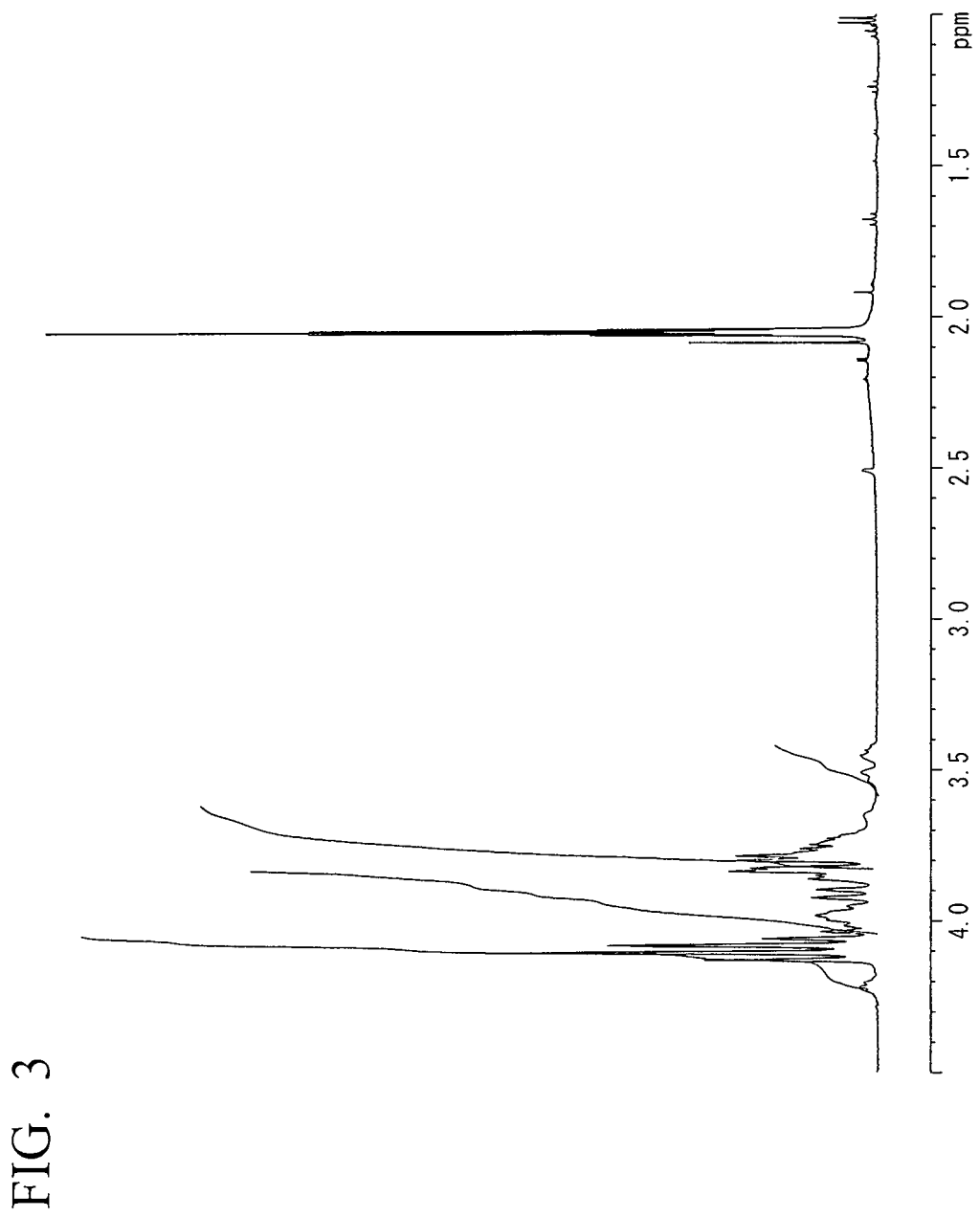
FIG. 3 is the $^1$H-NMR spectrum of the product obtained in Example 1.
Figure 4:
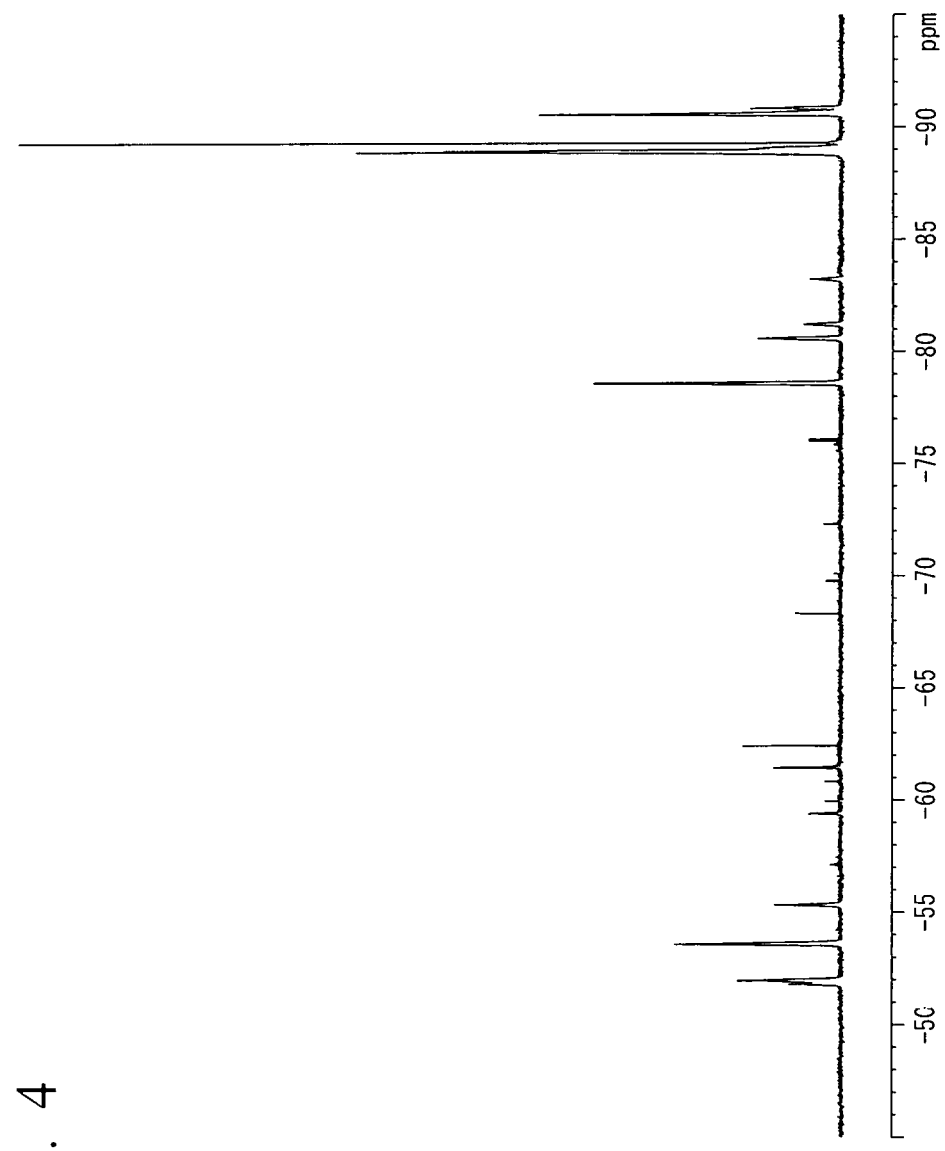
FIG. 4 is the $^{19}$F-NMR spectrum of the product obtained in Example 1.

$^{1}$H-NMR and $^{19}$F-NMR measurements of the obtained compound D; 3a were performed, and the structure was identified based on the following results. Further, the measured $^{1}$H-NMR and $^{19}$F-NMR spectra are shown in FIG. 3 and FIG. 4 respectively.

(Identification Data)

$^{1}$H-NMR (acetone-$D_6$): δ [ppm]=3.42 to 3.59 (2H), 3.61 to 3.33 (7H), 3.83 to 4.04 (8H), 4.04 to 4.28 (10H)

$^{19}$F-NMR (acetone-$D_6$): δ [ppm]=−91.15 to −88.51 (36F), −83.21 (1F), −81.22 (1F), −80.60 (3F), −78.81 to −78.45 (7F), −55.65 to −51.59 (12F)

[Chemical formula 50]

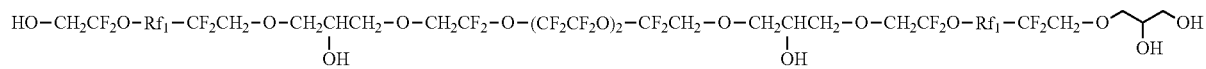

(D)

Subsequently, a fluorine-based solvent (product name: ASAHIKLIN (a registered trademark) AK-225, manufactured by Asahi Glass Co., Ltd.) was added to the round bottom flask, the product of the above reaction was washed with water and then collected, dewatered and filtered in the same manner as that described for the compound 3a represented by formula (D), and the resulting residue was then separated by column chromatography. The above steps yielded a colorless and transparent liquid compound F; 5a (2 g) represented by a formula (F) shown below. $Rf_1$ in the following formula (F) is represented by the formula (RF-1) shown above.

$^{1}$H-NMR and $^{19}$F-NMR measurements of the obtained compound F were performed, and the structure was identified based on the following results.

(Identification Data)

$^{1}$H-NMR (acetone-$D_6$): δ [ppm]=2.59 (1H), 2.76 (1H), 3.11 (1H), 3.56 (1H), 3.73 to 3.81 (4H), 3.81 to 4.18 (19H)

$^{19}$F-NMR (acetone-$D_6$): δ [ppm]=−91.15 to −88.51 (36F), −83.21 (1F), −81.22 (1F), −80.88 to −80.34 (3F), −78.93 to −78.30 (7F), −55.65 to −51.59 (12F)

[Chemical formula 51]

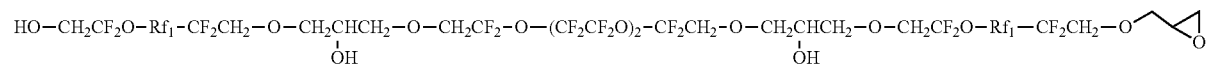

(F)

A 300 mL round bottom flask was charged, under a nitrogen atmosphere, with the compound 5a represented by formula (F) (1 g) and t-butanol (10 mL), and stirring was performed until a uniform mixture was obtained. Subsequently, ethylene glycol (1.5 mL) and potassium tert-butoxide (0.1 g) were added to the mixture, and the resulting mixture was stirred for 9 hours while heating at 70° C., and was then cooled to 25° C.

Subsequently, a fluorine-based solvent (product name: ASAHIKLIN (a registered trademark) AK-225, manufactured by Asahi Glass Co., Ltd.) was added to the round bottom flask, the product of the above reaction was washed with water and then collected, dewatered and filtered in the same manner as that described for the compound 3a represented by formula (D), and the resulting residue was then Example 2

(Synthesis of Compound)

A 300 mL round bottom flask was charged, under a nitrogen atmosphere, with the compound 2a represented by formula (B) (4 g) and t-butanol (40 mL), and stirring was performed until a uniform mixture was obtained. Next, epibromohydrin (2.9 mL) and potassium tert-butoxide (0.3 g) were added to the mixture, and the mixture was stirred for 9 hours while heating at 70° C., and was then cooled to 25° C.

separated by column chromatography. The above steps yielded a colorless and transparent liquid compound G; 7a (0.8 g) represented by a formula (G) shown below. $Rf_1$ in the following formula (G) is represented by the formula (RF-1) shown above.

$^{1}$H-NMR and $^{19}$F-NMR measurements of the obtained compound G were performed, and the structure was identified based on the following results.

(Identification Data)

$^{1}$H-NMR (acetone-$D_6$): δ [ppm]=3.46 to 3.63 (5H), 3.65 to 3.81 (7H), 3.81 to 4.18 (19H)

$^{19}$F-NMR (acetone-D$_6$): δ [ppm]=−91.15 to −88.51 (36F), −83.21 (1F), −81.22 (1F), −80.78 to −80.38 (3F), −78.80 to −78.38 (7F), −55.65 to −51.59 (12F)

[Chemical formula 52]

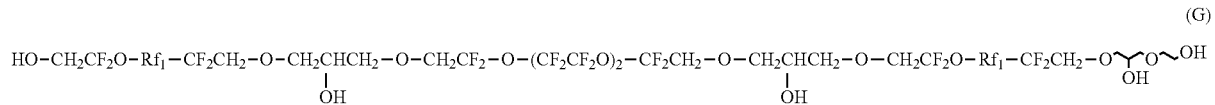

(G)

Example 3

A 300 mL round bottom flask was charged, under a nitrogen atmosphere, with the compound 5a represented by formula (F) (1 g) and t-butanol (10 mL), and stirring was performed until a uniform mixture was obtained. Subsequently, 2,2,3,3-fluorobutane-1,4-diol (3 g) and potassium tert-butoxide (0.1 g) were added to the mixture, and the resulting mixture was stirred for 9 hours while heating at 70° C., and was then cooled to 25° C.

Subsequently, a fluorine-based solvent (product name: ASAHIKLIN (a registered trademark) AK-225, manufactured by Asahi Glass Co., Ltd.) was added to the round bottom flask, the product of the above reaction was washed with water and then collected, dewatered and filtered in the same manner as that described for the compound 3a represented by formula (D), and the resulting residue was then separated by column chromatography. The above steps yielded a colorless and transparent liquid compound H; 9a (1.0 g) represented by a formula (H) shown below. Rf$_1$ in the following formula (H) is represented by the formula (RF-1) shown above.

$^1$H-NMR and $^{19}$F-NMR measurements of the obtained compound H were performed, and the structure was identified based on the following results.
(Identification Data)
$^1$H-NMR (acetone-D$_6$): δ [ppm]=3.67 to 4.05 (19H), 4.05 to 4.22 (12H)
$^{19}$F-NMR (acetone-D$_6$): δ [ppm]=−125.27 (2F), −123.31 (2F), −91.15 to −88.51 (36F), −83.21 (1F), −81.22 (1F), −80.78 to −80.38 (3F), −78.80 to −78.38 (7F), −55.65 to −51.59 (12F)

[Chemical formula 53]

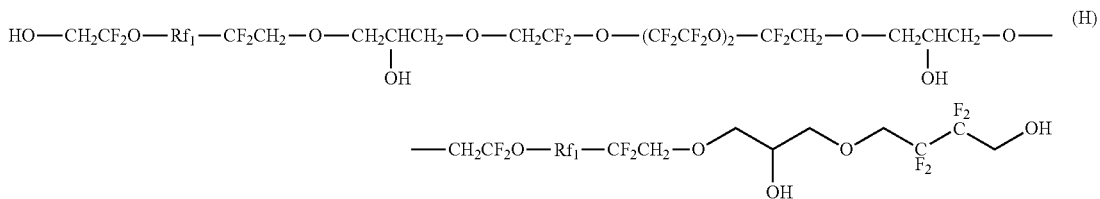

(H)

Example 4

A 500 mL round bottom flask was charged with 3-butenyl acetate (6.0 g), dichloromethane (100.0 mL) and sodium bicarbonate (8.7 g), and stirring was performed until a uniform mixture was obtained. Subsequently, the mixture was cooled in ice to 0° C., m-chloroperbenzoic acid (15.5 g) was added and stirred for one hour, and stirring was then continued at 25° C. for 6 hours, thus obtaining a reaction product. Next, the reaction product was cooled in ice to 0° C., a saturated aqueous solution of sodium bicarbonate (20 mL) and a saturated aqueous solution of sodium sulfite (20 mL) were added, and the mixture was stirred for 0.5 hours. Subsequently, the thus obtained reaction product was washed with water and then collected, dewatered and filtered in the same manner as that described for the compound 3a represented by formula (D), and the resulting residue was then separated by column chromatography. The above steps yielded a colorless and transparent liquid compound 11 (3.2 g) represented by a formula (I) shown below.

A $^1$H-NMR measurement of the obtained compound 11 was performed, and the structure was identified based on the following results.
(Identification Data)
$^1$H-NMR (acetone-$D_6$): δ [ppm]=1.73 (1H), 1.88 (1H), 2.01 (3H), 2.41 (1H), 2.67 (1H), 2.88 (1H), 4.12 (2H)

[Chemical formula 54]

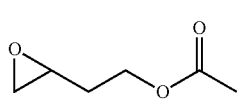

(I)

A 100 mL round bottom flask was charged, under a nitrogen atmosphere, with the compound 2a represented by formula (B) (6.3 g), t-butanol (63 mL), and the compound 11 represented by formula (1) (0.3 mL), and stirring was performed until a uniform mixture was obtained. Subsequently, potassium tert-butoxide (0.59 g) was added to the mixture, and the mixture was stirred for 7 hours while heating at 70° C., and was then cooled to 25° C.

Subsequently, a fluorine-based solvent (product name: ASAHIKLIN (a registered trademark) AK-225, manufactured by Asahi Glass Co., Ltd.) was added to the round bottom flask, the product of the above reaction was washed with water and then collected, dewatered and filtered in the same manner as that described for the compound 3a represented by formula (D), and the resulting residue was then separated by column chromatography. The above steps yielded a colorless and transparent liquid compound J; 12a (3.4 g) represented by a formula (0.1) shown below. $Rf_1$ in the following formula (J) is represented by the formula (RF-1) shown above.

$^1$H-NMR and $^{19}$F-NMR measurements of the obtained compound J were performed, and the structure was identified based on the following results.
(Identification Data)
$^1$H-NMR (acetone-$D_6$): δ [ppm]=1.54 to 1.76 (2H), 3.42 to 3.59 (2H), 3.61 to 3.83 (7H), 3.83 to 4.04 (8H), 4.04 to 4.28 (10H)
$^{19}$F-NMR (acetone-$D_6$): δ [ppm]=−91.15 to −88.51 (36F), −83.21 (1F), −81.22 (1F), −80.78 to −80.38 (3F), −78.80 to −78.38 (7F), −55.65 to −51.59 (12F)

[Chemical formula 55]

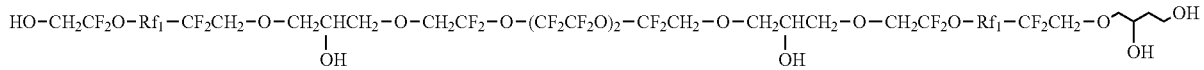

(J)

Example 5

A 300 mL round bottom flask was charged, under a nitrogen atmosphere, with the compound 5a represented by formula (F) (1 g) and t-butanol (10 mL), and stirring was performed until a uniform mixture was obtained. Subsequently, propanediol (1.5 mL) and potassium tert-butoxide (0.1 g) were added to the mixture, and the resulting mixture was stirred for 9 hours while heating at 70° C., and was then cooled to 25° C.

Subsequently, a fluorine-based solvent (product name: ASAHIKLIN (a registered trademark) AK-225, manufactured by Asahi Glass Co., Ltd.) was added to the round bottom flask, the product of the above reaction was washed with water and then collected, dewatered and filtered in the same manner as that described for the compound 3a represented by formula (D), and the resulting residue was then separated by column chromatography. The above steps yielded a colorless and transparent liquid compound K; 14a (0.8 g) represented by a formula (K) shown below. $Rf_1$ in the following formula (K) is represented by the formula (RF-1) shown above.

$^1$H-NMR and $^{19}$F-NMR measurements of the obtained compound K were performed, and the structure was identified based on the following results.
(Identification Data)
$^1$H-NMR (acetone-$D_6$): δ [ppm]=1.79 (2H), 3.46 to 3.63 (5H), 3.65 to 3.81 (7H), 3.81 to 4.18 (19H)

$^{19}$F-NMR (acetone-D$_6$): δ [ppm]=−91.15 to −88.51 (36F), −83.21 (1F), −81.22 (1F), −80.78 to −80.38 (3F), −78.80 to −78.38 (7F), −55.65 to −51.59 (12F)

[Chemical formula 56]

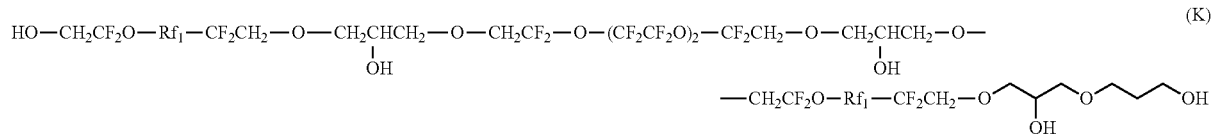

(K)

Example 6

With the exception of adding butanediol (1.5 mL) together with the potassium tert-butoxide instead of the propanediol used in Example 5, a colorless and transparent liquid compound L; 16a (0.8 g) represented by a formula (L) shown below was obtained in the same manner as Example 5. Rf$_1$ in the following formula (L) is represented by the formula (RF-1) shown above.

$^1$H-NMR and $^{19}$F-NMR measurements of the obtained compound 16a were performed, and the structure was identified based on the following results.
(Identification Data)

$^1$H-NMR (acetone-D$_6$): δ [ppm]=1.61 (2H), 1.71 (2H), 3.46 to 3.63 (5H), 3.65 to 3.81 (7H), 3.81 to 4.18 (19H)

$^{19}$F-NMR (acetone-D$_6$): δ [ppm]=−91.15 to −88.51 (36F), −83.21 (1F), −81.22 (1F), −80.78 to −80.38 (3F), −78.80 to −78.38 (7F), −55.65 to −51.59 (12F)

[Chemical formula 57]

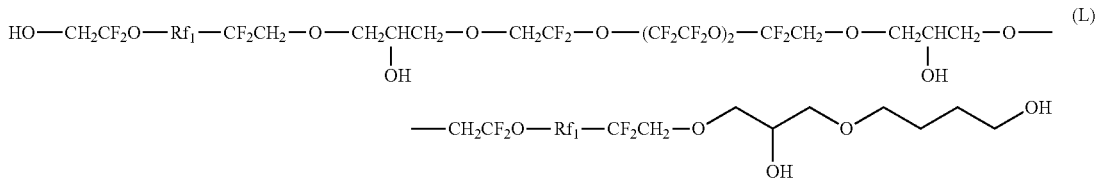

(L)

Example 7

A 100 mL round bottom flask was charged, under a nitrogen atmosphere, with the compound 1a represented by formula (A) (1 g) and a fluoropolyether represented by HOCH$_2$CF$_2$O(CF$_2$CF$_2$O)$_m$CF$_2$CH$_2$OH (wherein m=1 to 9, number average molecular weight: 800, molecular weight distribution: 1.02) (28 g), and stirring was performed until a uniform mixture was obtained. Subsequently, 0.8 g of potassium carbonate was added to the mixture, and the mixture was stirred for 8 hours while heating at 70° C., and was then cooled to 25° C.

Subsequently, a neutralization was performed by adding hydrochloric acid to the round bottom flask, and water washing, collection, dewatering, filtering and extraction were then performed in the same manner as that described for the compound 2a represented by formula (B) in Example 1. The above steps yielded a colorless and transparent liquid compound 2b (3 g) represented by a formula (M). Rf$_2$ in the following formula (M) is represented by a formula (RF-2) shown below.

$^1$H-NMR and $^{19}$F-NMR measurements of the obtained compound 2b were performed, and the structure was identified based on the following results.
(Identification Data)

$^1$H-NMR (acetone-D$_6$): δ [ppm]=3.71 to 3.81 (4H), 3.80 to 4.02 (10H), 4.05 to 4.20 (8H)

$^{19}$F-NMR (acetone-D$_6$): δ [ppm]=−91.15 to −88.51 (48F), −81.40 to −80.85 (4F), −78.81 to −78.45 (8F)

[Chemical formula 58]

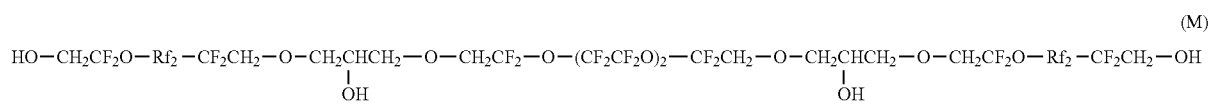

(M)

[Chemical formula 59]

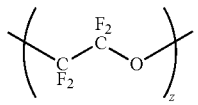
(RF-2)

(In formula (RF-2), z represents an integer of 1 to 9.)

Next, a 50 mL round bottom flask was charged, under a nitrogen atmosphere, with the compound 2b represented by formula (M) (4 g) and t-butanol (40 mL), and stirring was performed until a uniform mixture was obtained. Subsequently, potassium tert-butoxide (0.5 g) was added to the mixture, and with the mixture undergoing stirring at 70° C., glycidol (250 μL) was added, and the resulting mixture was then stirred for 8 hours, and then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the resulting residue was then separated by column chromatography. The above steps yielded a colorless and transparent liquid compound O; 3b (1.7 g) represented by a formula (O). $Rf_2$ in the following formula (O) is represented by the formula (RF-2) shown above.

$^1$H-NMR and $^{19}$F-NMR measurements of the obtained compound 0 were performed, and the structure was identified based on the following results.
(Identification Data)

$^1$H-NMR (acetone-$D_6$): δ [ppm]=3.71 to 3.81 (8H), 3.80 to 4.02 (11H), 4.05 to 4.20 (8H)

$^{19}$F-NMR (acetone-$D_6$): δ [ppm]=−91.15 to −88.51 (48F), −81.40 to −80.85 (2F), −78.81 to −78.45 (10F)

[Chemical formula 60]

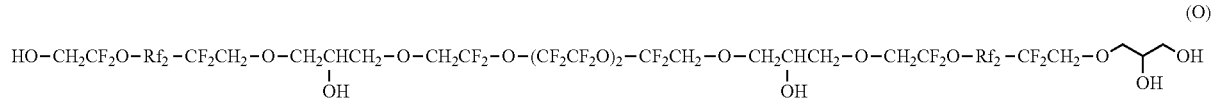
(O)

Example 8

With the exception of using the compound 2b represented by formula (M) instead of the compound 2a represented by formula (B), a colorless and transparent liquid compound 5b (2 g) represented by a formula (P) shown below was obtained in the same manner as the compound 5a represented by formula (F) in Example 2. $Rf_2$ in the following formula (P) is represented by the formula (RF-2) shown above.

$^1$H-NMR and $^{19}$F-NMR measurements of the obtained compound 5b were performed, and the structure was identified based on the following results.
(Identification Data)

$^1$H-NMR (acetone-$D_6$): δ [ppm]=2.59 (1H), 2.76 (1H), 3.11 (1H), 3.56 (1H), 3.71 to 4.02 (151-1), 4.05 to 4.20 (8H)

$^{19}$F-NMR (acetone-$D_6$): δ [ppm]=−91.15 to −88.51 (48F), −81.40 to −80.85 (2F), −78.81 to −78.45 (10F)

[Chemical formula 61]

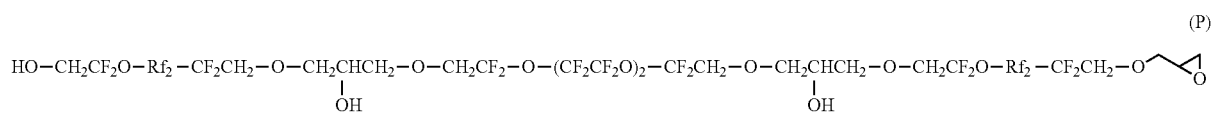
(P)

With the exception of using the compound 5b represented by formula (P) instead of the compound 5a represented by formula (F), a colorless and transparent liquid compound Q; 7b (2 g) represented by a formula (Q) shown below was obtained in the same manner as the compound 7a represented by formula (G) in Example 2. $Rf_2$ in the following formula (Q) is represented by the formula (RF-2) shown above.

$^1$H-NMR and $^{19}$F-NMR measurements of the obtained compound Q were performed, and the structure was identified based on the following results.
(Identification Data)
$^1$H-NMR (acetone-$D_6$): δ [ppm]=3.45 to 3.65 (5H), 3.70 to 3.80 (7H), 3.80 to 4.20 (19H)
$^{19}$F-NMR (acetone-$D_6$): δ [ppm]=−91.15 to −88.51 (48F), −81.40 to −80.85 (2F), −78.81 to −78.45 (10F)

[Chemical formula 62]

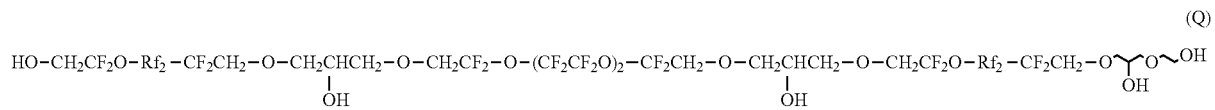

(Q)

Example 9

With the exceptions of using the compound 5b represented by formula (P) instead of the compound 5a represented by formula (F), and altering the amount used of the potassium tert-butoxide to 0.15 g, a colorless and transparent liquid compound R; 9b (1.0 g) represented by a formula (R) shown below was obtained in the same manner as the compound 9a represented by formula (H) in Example 3. $Rf_1$ in the following formula (R) is represented by the formula (RF-2) shown above.

$^1$H-NMR and $^{19}$F-NMR measurements of the obtained compound R were performed, and the structure was identified based on the following results.
(Identification Data)
$^1$H-NMR (acetone-$D_6$): δ [ppm]=3.65 to 4.07 (19H), 4.07 to 4.25 (12H)
$^{19}$F-NMR (acetone-$D_6$): δ [ppm]=−125.27 (2F), −123.31 (2F), −91.15 to −88.51 (48F), −81.40 to −80.85 (2F), −78.81 to −78.45 (10F)

[Chemical formula 63]

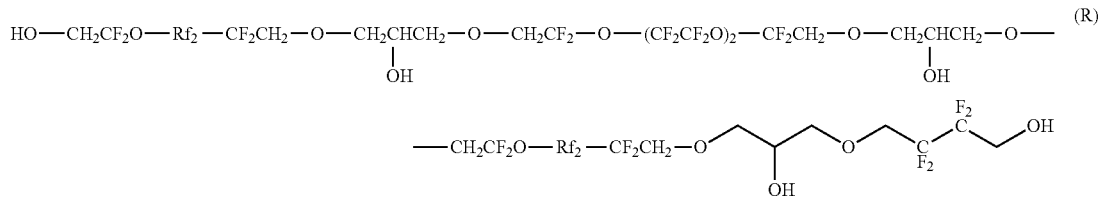

(R)

Example 10

With the exception of using 1H,1H,11H,11H-octafluoro-3,6-dioxaoctane-1,8-diol instead of 1H,1H,11H,11H-dodecafluoro-3,6,9-trioxaundecane-1,11-diol, a colorless and transparent liquid compound 1c (18 g) represented by a formula (S) shown below was obtained in the same manner as that described for the compound 1a represented by formula (A) in Example 1.

$^1$H-NMR and $^{19}$F-NMR measurements of the obtained compound 1c were performed, and the structure was identified based on the following results.

(Identification Data)
$^1$H-NMR (acetone-$D_6$): δ [ppm]=2.60 (2H), 2.77 (2H), 3.15 (2H), 3.56 (2H), 4.04 (6H)
$^{19}$F-NMR (acetone-$D_6$): δ [ppm]=−89.50 to −89.00 (4F), −79.00 to −78.70 (4F)

[Chemical formula 64]

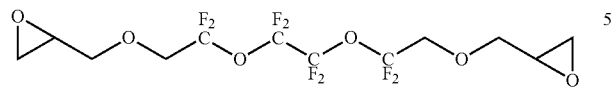
(S)

With the exception of using the compound 1c represented by formula (S) instead of the compound 1a represented by formula (A), a colorless and transparent liquid compound 2c (3 g) represented by a formula (T) shown below was obtained in the same manner as the compound 2a represented by formula (B) in Example 1. $Rf_1$ in the following formula (T) is represented by the formula (RF-1) shown above.

$^1$H-NMR and $^{19}$F-NMR measurements of the obtained compound 2c were performed, and the structure was identified based on the following results.
(Identification Data)
$^1$H-NMR (acetone-$D_6$): δ [ppm]=3.74 to 3.81 (4H), 3.81 to 4.02 (10H), 4.04 in 4.16 (8H)
$^{19}$F-NMR (acetone-$D_6$): δ [ppm]=−91.15 to −88.51 (32F), −83.19 (2F), −81.23 (2F), −80.61 (2F), −78.81 to −78.45 (6F), −55.65 to −51.59 (12F)

[Chemical formula 65]

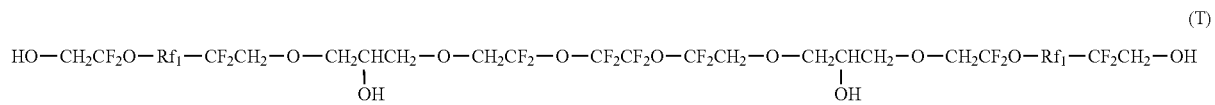
(T)

With the exception of using the compound 2c represented by formula (T) instead of the compound 2a represented by formula (B), a colorless and transparent liquid compound U; 3c (3 g) represented by a formula (U) shown below was obtained in the same manner as the compound 3a represented by formula (D) in Example 1. $Rf_1$ in the following formula (U) is represented by the formula (RF-1) shown above.

$^1$H-NMR and $^{19}$F-NMR measurements of the obtained compound U were performed, and the structure was identified based on the following results.
(Identification Data)
$^1$H-NMR (acetone-$D_6$): δ [ppm]=3.42 to 3.59 (2H), 3.61 to 3.83 (7H), 3.83 to 4.04 (8H), 4.04 to 4.28 (10H)
$^{19}$F-NMR (acetone-De): δ [ppm]=−91.15 to −88.51 (32F), −83.21 (1F), −81.22 (1F), −80.60 (3F), −78.81 to −78.45 (7F), −55.65 to −51.59 (12F)

[Chemical formula 66]

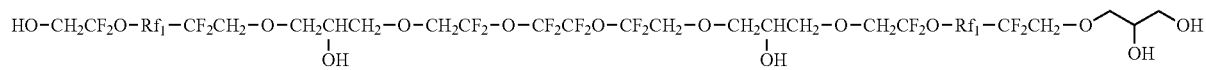
(U)

Example 11

A 500 mL round bottom flask was charged, under a nitrogen atmosphere, with a fluoropolyether represented by $HOCH_2CF_2O(CH_2CF_2O)_m(CF_2O)_nCF_2CH_2OH$ (wherein m=1 to 7, n=1 to 7, number average molecular weight: 800, molecular weight distribution: 1.1) (10 g), t-butanol (15 mL) and potassium tert-butoxide (1.0 g), thus forming a mixture. The thus obtained mixture was stirred for one hour while heating at 70° C.

Next, epibromohydrin (4.0 g) was added dropwise to the above mixture, and the resulting mixture was stirred for 5 hours while heating at 70° C., and was then cooled to 25° C. Subsequently, a fluorine-based solvent (product name: ASAHIKLIN (a registered trademark) AK-225, manufactured by Asahi Glass Co., Ltd.) was added to the round bottom flask, the product of the above reaction was washed with water and then collected, dewatered and filtered in the same manner as that described for the compound 3a represented by formula (D), and the resulting residue was then separated by column chromatography. The above steps yielded a colorless and transparent liquid compound 18a (8.0 g) represented by a formula (V).

$^1$H-NMR and $^{19}$F-NMR measurements of the obtained compound 18a were performed, and the structure was identified based on the following results.

(Identification Data)

$^1$H-NMR (acetone-$D_6$): δ [ppm]=2.60 (2H), 2.77 (2H), 3.12 (2H), 3.57 (2H), 3.70 to 4.29 (6H)

$^{19}$F-NMR (acetone-$D_6$): δ [ppm]=−91.15 to −88.51 (14F), −80.61 (2F), −78.75 (2F), −55.65 to −51.59 (6F)

[Chemical formula 67]

$$\text{O}\diagdown\!\!\!\diagup\!\!\text{OCH}_2\text{CF}_2\text{O}-(\text{CF}_2\text{CF}_2\text{O})_x(\text{CF}_2\text{O})_y-\text{CF}_2\text{CH}_2-\text{O}\diagdown\!\!\!\diagup\!\!\text{O} \quad (V)$$

(In formula (V), x represents an integer of 1 to 7, an y represents an integer of 1 to 7.)

With the exceptions of using the compound 18a represented by formula (V) instead of the compound 1a represented by formula (A), and altering the amount used of the fluoropolyether represented by $HOCH_2CF_2O(CF_2CF_2O)_x(CF_2O)_yCF_2CH_2OH$ (wherein x=1 to 7, y=1 to 7, number average molecular weight: 800, molecular weight distribution: 1.1) to 20 g, a colorless and transparent liquid compound 19a (2.4 g) represented by a formula (W) shown below was obtained in the same manner as the compound 2a represented by formula (B) in Example 1. $Rf_1$ in the following formula (W) is represented by the formula (RF-1) shown above.

$^1$H-NMR and $^{19}$F-NMR measurements of the obtained compound 19a were performed, and the structure was identified based on the following results.

(Identification Data)

$^1$H-NMR (acetone-$D_6$): δ [ppm]=3.74 to 3.81 (4H), 3.81 to 4.16 (18H)

$^{19}$F-NMR (acetone-$D_6$): δ [ppm]=−91.15 to −88.51 (42F), −83.20 (2F), −81.25 (2F), −80.61 (4F), −78.75 (4F), −55.65 to −51.59 (18F)

[Chemical formula 68]

$$HO-CH_2CF_2O-Rf_1-CF_2CH_2-O-CH_2\underset{\underset{OH}{|}}{CH}CH_2-O-CH_2CF_2-O-Rf_1-CF_2CH_2-O-CH_2\underset{\underset{OH}{|}}{CH}CH_2-O-CH_2CF_2O-Rf_1-CF_2CH_2-OH \quad (W)$$

With the exception of using the compound 19a represented by formula (W) (3.5 g) instead of the compound 2a represented by formula (B) (4 g), a colorless and transparent liquid compound X; 20a (2.0 g) represented by a formula (X) shown below was obtained in the same manner as the compound 3a represented by formula (D) in Example 1. $Rf_1$ in the following formula (X) is represented by the formula (RF-1) shown above.

$^1$H-NMR and $^{19}$F-NMR measurements of the obtained compound X were performed, and the structure was identified based on the following results.

(Identification Data)

$^1$H-NMR (acetone-$D_6$): δ [ppm]=3.41 to 3.81 (9H), 3.81 to 4.16 (18H)

$^{19}$F-NMR (acetone-$D_6$): δ [ppm]=−91.15 to −88.51 (42F), −83.20 (1F), −81.25 (1F), −80.61 (5F), −78.75 (5F), −55.65 to −51.59 (18F)

[Chemical formula 69]

$$HO\diagdown\!\!\underset{\underset{OH}{|}}{\diagup}O-CH_2CF_2O-Rf_1-CF_2CH_2-O-CH_2\underset{\underset{OH}{|}}{CH}CH_2-O-CH_2CF_2-O-Rf_1-CF_2CH_2-O-CH_2\underset{\underset{OH}{|}}{CH}CH_2-O-CH_2CF_2O-Rf_1-CF_2CH_2-OH \quad (X)$$

Example 12

With the exception of using the compound 19a represented by formula (W) instead of the compound 2a represented by formula (B), a colorless and transparent liquid compound 22a (2 g) represented by a formula (Y) shown below was obtained in the same manner as the compound 5a represented by formula (F) in Example 2. $Rf_1$ in the following formula (Y) is represented by the formula (RF-1) shown above.

$^1$H-NMR and $^{19}$F-NMR measurements of the obtained compound 22a were performed, and the structure was identified based on the following results.

(Identification Data)

$^1$H-NMR (acetone-$D_6$): δ [ppm]=2.59 (1H), 2.76 (1H), 3.11 (1H), 3.41 to 3.81 (61-), 3.81 to 4.16 (18H)

$^{19}$F-NMR (acetone-$D_6$): δ [ppm]=−91.15 to −88.51 (42F), −83.21 (1F), −81.22 (1F), −80.88 to −80.34 (5F), −78.93 to −78.30 (5F), −55.65 to −51.59 (18F)

[Chemical formula 70]

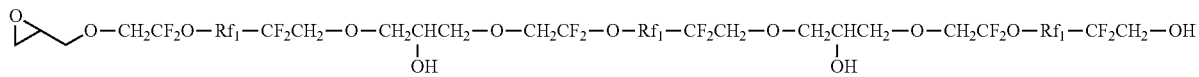

(Y)

With the exception of using the compound 22a represented by formula (Y) instead of the compound 5a represented by formula (F), a colorless and transparent liquid compound Z; 24a (0.7 g) represented by a formula (Z) shown below was obtained in the same manner as the compound 7a represented by formula (G) in Example 2. $Rf_1$ in the following formula (Z) is represented by the formula (RF-1) shown above.

$^1$H-NMR and $^{19}$F-NMR measurements of the obtained compound Z were performed, and the structure was identified based on the following results.

(Identification Data)

$^1$H-NMR (acetone-$D_6$): δ [ppm]=3.46 to 3.63 (5H), 3.65 to 3.81 (7H), 3.81 to 4.18 (19H)

$^{19}$F-NMR (acetone-$D_6$): δ [ppm]=−91.15 to −88.51 (42F), −83.21 (1F), −81.22 (1F), −80.88 to −80.34 (5F), −78.93 to −78.30 (5F), −55.65 to −51.59 (18F)

[Chemical formula 71]

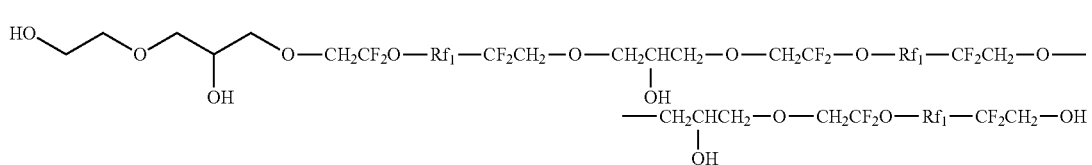

(Z)

Comparative Example 1

The compound B; 2a represented by formula (B) and synthesized in Example 1 was used.

Comparative Example 2

A 300 mL round bottom flask was charged, under a nitrogen atmosphere, with the compound 2a represented by formula (B) (4 g) and t-butanol (40 mL), and stirring was performed until a uniform mixture was obtained. Subsequently, potassium tert-butoxide (0.1 g) was added to the mixture, and with the mixture undergoing stirring at 70° C., glycidol (250 μL) was added, and the resulting mixture was then stirred for 8 hours, and then cooled to 25° C.

Subsequently, a fluorine-based solvent (product name: ASAHIKLIN (a registered trademark) AK-225, manufactured by Asahi Glass Co., Ltd.) was added to the above round bottom flask, the product of the above reaction was washed with water and then collected, dewatered and filtered in the same manner as that described for the compound 3a represented by formula (D), and the resulting residue was then separated by column chromatography. The above steps yielded a colorless and transparent liquid compound AA; 4a (0.9 g) represented by a formula (AA) shown below. $Rf_1$ in the following formula (AA) is represented by the formula (RF-1) shown above.

$^1$H-NMR and $^{19}$F-NMR measurements of the obtained compound AA were performed, and the structure was identified based on the following results.

(Identification Data)

$^1$H-NMR (acetone-$D_6$): δ [ppm]=3.42 to 3.59 (2H), 3.61 to 3.83 (9H), 3.83 to 4.04 (9H), 4.04 to 4.28 (12H)

$^{19}$F-NMR (acetone-$D_6$): δ [ppm]=−91.15 to −88.51 (36F), −80.60 (4F), −78.81 to −78.45 (8F), −55.65 to −51.59 (12F)

[Chemical formula 72]

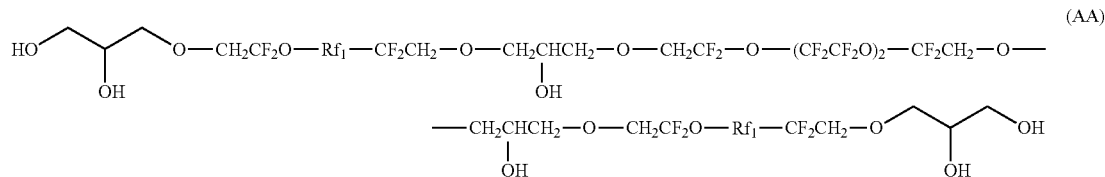

(AA)

Comparative Example 3

A 300 mL round bottom flask was charged, under a nitrogen atmosphere, with the compound 2a represented by formula (B) (4 g) and t-butanol (40 mL), and stirring was performed until a uniform mixture was obtained. Subsequently, epibromohydrin (2.9 mL) and potassium tert-butoxide (0.3 g) were added to the mixture, and the resulting mixture was stirred for 9 hours while heating at 70° C., and was then cooled to 25° C.

Subsequently, a fluorine-based solvent (product name: ASAHIKLIN (a registered trademark) AK-225, manufactured by Asahi Glass Co., Ltd.) was added to the above round bottom flask, the product of the above reaction was washed with water and then collected, dewatered and filtered in the same manner as that described for the compound 3a represented by formula (D), and the resulting residue was then separated by column chromatography. The above steps yielded a colorless and transparent liquid compound 6a (0.7 g) represented by a formula (AB) shown below. $Rf_1$ in the following formula (AB) is represented by the formula (RF-1) shown above.

$^1$H-NMR and $^{19}$F-NMR measurements of the obtained compound 6a were performed, and the structure was identified based on the following results.

(Identification Data)

$^1$H-NMR (acetone-$D_6$): δ [ppm]=2.59 (2H), 2.76 (2H), 3.11 (2H), 3.56 (2H), 3.73 to 3.81 (5H), 3.81 to 4.18 (19H)

$^{19}$F-NMR (acetone-$D_6$): δ [ppm]=−91.15 to −88.51 (36F), −80.88 to −80.34 (4F), −78.93 to −78.30 (8F), −55.65 to −51.59 (12F)

[Chemical formula 73]

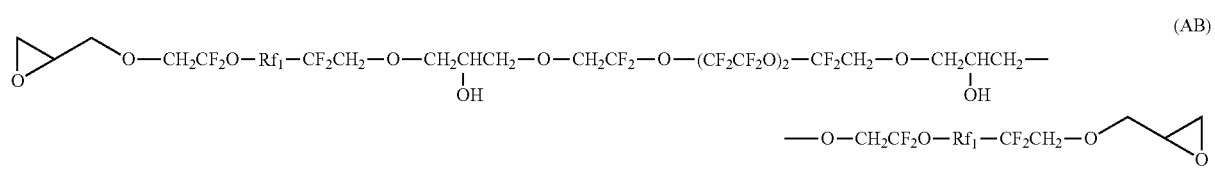

(AB)

A 300 mL round bottom flask was charged, under a nitrogen atmosphere, with the compound 6a represented by formula (AB) (4 g) and t-butanol (10 mL), and stirring was performed until a uniform mixture was obtained. Subsequently, ethylene glycol (2 mL) and potassium tert-butoxide (0.15 g) were added to the mixture, and the resulting mixture was stirred for 9 hours while heating at 70° C., and was then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the resulting residue was then separated by column chromatography. The above steps yielded a colorless and transparent liquid compound AC; 8a (0.7 g) represented by a formula (AC) shown below. $Rf_1$ in the following formula (AC) is represented by the formula (RF-1) shown above.

$^1$H-NMR and $^{19}$F-NMR measurements of the obtained compound AC were performed, and the structure was identified based on the following results.

(Identification Data)

$^1$H-NMR (acetone-$D_6$): δ [ppm]=3.46 to 3.63 (8H), 3.65 to 3.81 (10H), 3.81 to 4.18 (22H)

$^{19}$F-NMR (acetone-$D_6$): δ [ppm]=−91.15 to −88.51 (36F), −80.78 to −80.38 (4F), −78.80 to −78.38 (8F), −55.65 to −51.59 (12F)

[Chemical formula 74]

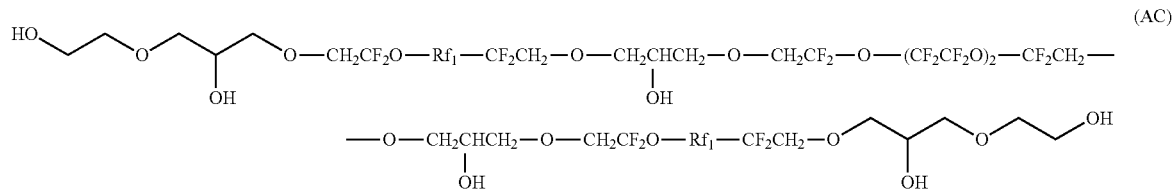

(AC)

Comparative Example 4

A 300 mL round bottom flask was charged, under a nitrogen atmosphere, with the compound 6a represented by formula (AB) (4 g) and t-butanol (10 mL), and stirring was performed until a uniform mixture was obtained. Subsequently, 2,2,3,3-fluorobutane-1,4-diol (5 g) and potassium tert-butoxide (0.15 g) were added to the mixture, and the resulting mixture was stirred for 9 hours while heating at 70° C., and was then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the residue was then separated by column chromatography. The above steps yielded a colorless and transparent liquid compound AD; 10a (0.7 g) represented by a formula (AD). $Rf_1$ in the following formula (AD) is represented by the formula (RF-1) shown above.

$^1$H-NMR and $^{19}$F-NMR measurements of the obtained compound AD were performed, and the structure was identified based on the following results.

(Identification Data)

$^1$H-NMR (acetone-$D_6$): δ [ppm]=3.67 to 4.05 (24H), 4.05 to 4.22 (16H)

$^{19}$F-NMR (acetone-$D_6$): δ [ppm]=−125.27 (4F), −123.31 (4F), −91.15 to −88.51 (36F), −83.21 (1F), −81.22 (1F), −80.78 to −80.38 (3F), −78.80 to −78.38 (7F), −55.65 to −51.59 (12F)

[Chemical formula 75]

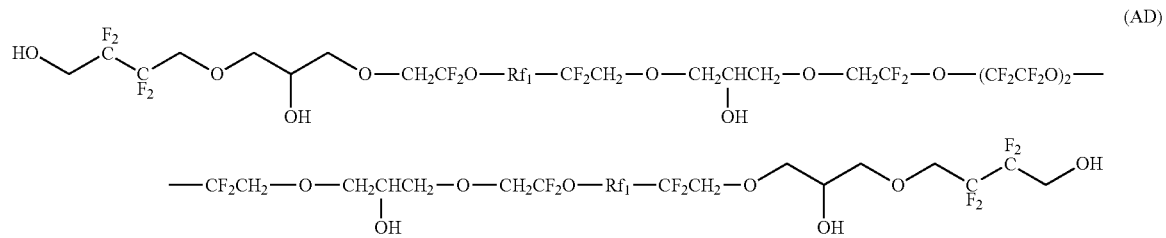

(AD)

Comparative Example 5

A 100 mL round bottom flask was charged, under a nitrogen atmosphere, with the compound 2a represented by formula (B) (6.3 g) and the compound 11 represented by formula (1) (0.3 mL), and stirring was performed until a uniform mixture was obtained. Subsequently, potassium tert-butoxide (0.59 g) was added to the mixture, and the resulting mixture was stirred for 7 hours while heating at 70° C., and was then cooled to 25° C.

Subsequently, a fluorine-based solvent (product name: ASAHIKLIN (a registered trademark) AK-225, manufactured by Asahi Glass Co., Ltd.) was added to the round bottom flask, the product of the above reaction was washed with water and then collected, dewatered and filtered in the same manner as that described for the compound 3a represented by formula (D), and the resulting residue was then separated by column chromatography. The above steps yielded a colorless and transparent liquid compound AE; 13a (1.0 g) represented by a formula (AE) shown below. $Rf_1$ in the following formula (AE) is represented by the formula (RF-1) shown above.

$^1$H-NMR and $^{19}$F-NMR measurements of the obtained compound AE were performed, and the structure was identified based on the following results.

(Identification Data)

$^1$H-NMR (acetone-$D_6$): δ [ppm]=1.54 to 1.76 (4H), 3.42 to 3.59 (2H), 3.61 to 3.83 (9H), 3.83 to 4.04 (9H), 4.04 to 4.28 (12H)

$^{19}$F-NMR (acetone-$D_6$): δ [ppm]=−91.15 to −88.51 (36F), −80.78 to −80.38 (4F), −78.80 to −78.38 (8F), −55.65 to −51.59 (12F)

[Chemical formula 76]

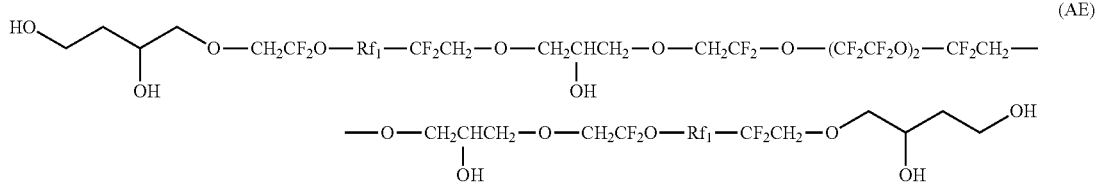

(AE)

Comparative Example 6

A 300 mL round bottom flask was charged, under a nitrogen atmosphere, with the compound 6a represented by formula (AB) (4 g) and t-butanol (10 mL), and stirring was performed until a uniform mixture was obtained. Subsequently, propanediol (2 mL) and potassium tert-butoxide (0.15 g) were added to the mixture, and the resulting mixture was stirred for 9 hours while heating at 70° C., and was then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the residue was then separated by column chromatography. The above steps yielded a colorless and transparent liquid compound AF; 15a (0.7 g) represented by a formula (AF). $Rf_1$ in the following formula (AF) is represented by the formula (RF-1) shown above.

$^1$H-NMR and $^{19}$F-NMR measurements of the obtained compound AF were performed, and the structure was identified based on the following results.

(Identification Data)

$^1$H-NMR (acetone-$D_6$): δ [ppm]=1.79 (4H), 3.46 to 3.63 (8H), 3.65 to 3.81 (10H), 3.81 to 4.18 (22H)

$^{19}$F-NMR (acetone-$D_6$): δ [ppm]=−91.15 to −88.51 (36F), −80.78 to −80.38 (4F), −78.80 to −78.38 (8F), −55.65 to −51.59 (12F)

[Chemical formula 77]

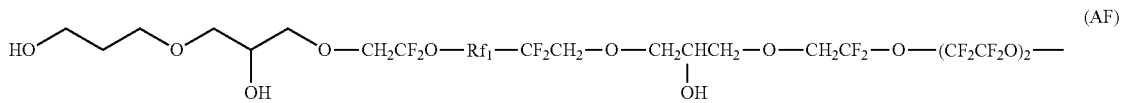

(AF)

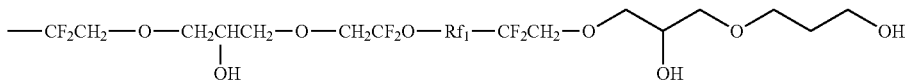

Comparative Example 7

With the exception of adding butanediol together with the potassium tert-butoxide instead of the propanediol used in Comparative Example 6, a colorless and transparent liquid compound AG; 17a (0.7 g) represented by a formula (AG) shown below was obtained in the same manner as Comparative Example 6. $Rf_1$ in the following formula (AG) is represented by the formula (RF-1) shown above.

$^1$H-NMR and $^{19}$F-NMR measurements of the obtained compound AG were performed, and the structure was identified based on the following results.

(Identification Data)

$^1$H-NMR (acetone-$D_6$): δ [ppm]=1.61 (4H), 1.71 (4H), 3.46 to 3.63 (8H), 3.65 to 3.81 (10H), 3.81 to 4.18 (22H)

$^{19}$F-NMR (acetone-$D_6$): δ [ppm]=−91.15 to −88.51 (36F), −80.78 to −80.38 (4F), −78.80 to −78.38 (8F),

[Chemical formula 78]

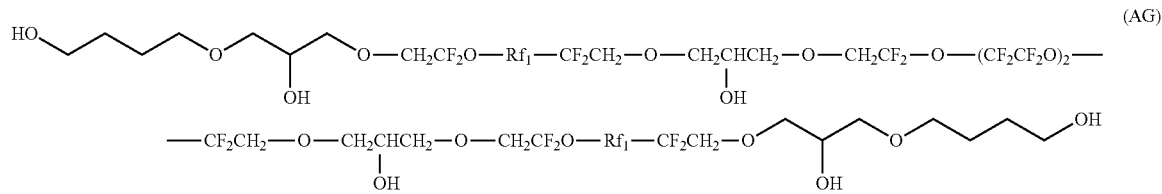

(AG)

Comparative Example 8

The compound M; 2b represented by formula (M) and synthesized in Example 7 was used.

Comparative Example 9

A 100 mL round bottom flask was charged, under a nitrogen atmosphere, with the compound 1a represented by formula (A) (1 g) and 1H,1H,11H,11H-dodecafluoro-3,6,9-trioxaundecane-1,11-diol, and stirring was performed until a uniform mixture was obtained. Subsequently, potassium carbonate (0.8 g) was added to the mixture, and the resulting mixture was stirred for 8 hours while heating at 70° C., and was then cooled to 25° C.

Subsequently, a neutralization was performed by adding hydrochloric acid to the round bottom flask, water washing, collection, dewatering, filtering and extraction were then performed in the same manner as that described for the compound 2a represented by formula (B) in Example 1. The above steps yielded a colorless and transparent liquid compound AH; 12b (0.7 g) represented by a formula (AH). Rf in the following formula (AH) is represented by $(CF_2CF_2O)_2$.

$^1$H-NMR and $^{19}$F-NMR measurements of the obtained compound AH were performed, and the structure was identified based on the following results.

(Identification Data)

$^1$H-NMR (acetone-$D_6$): δ [ppm]=3.80 (4H), 3.87 (4H), 3.95 (4H), 4.01 (2H), 4.11 (4H), 4.14 (4H)

$^{19}$F-NMR (acetone-$D_6$): δ [ppm]=−89.31 (12F), −88.98 (12F), −81.12 (4F), −78.59 (8F)

[Chemical formula 79]

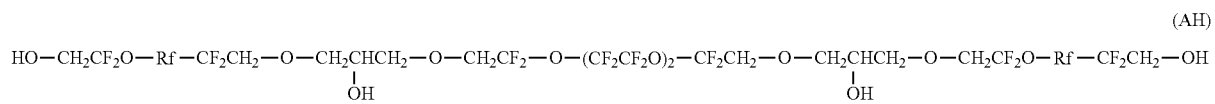

(AH)

Comparative Example 10

A 50 mL round bottom flask was charged, under a nitrogen atmosphere, with the compound 2b represented by formula (M) (4 g) and t-butanol (40 mL), and stirring was performed until a uniform mixture was obtained. Subsequently, potassium tert-butoxide (0.5 g) was added to the mixture, and with the mixture undergoing stirring at 70° C., glycidol (250 μL) was added, and the resulting mixture was then stirred for 8 hours, and then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the residue was then separated by column chromatography. The above steps yielded a colorless and transparent liquid compound AJ; 4b (1.0 g) represented by a formula (AJ). $Rf_2$ in the following formula (AJ) is represented by the formula (RF-2) shown above.

$^1$H-NMR and $^{19}$F-NMR measurements of the obtained compound AJ were performed, and the structure was identified based on the following results.

(Identification Data)

$^1$H-NMR (acetone-$D_6$): δ [ppm]=3.71 to 3.81 (12H), 3.80 to 4.02 (12H), 4.05 to 4.20 (8H)

$^{19}$F-NMR (acetone-$D_6$): δ [ppm]=−91.15 to −88.51 (48F), −78.81 to −78.45 (12F)

[Chemical formula 80]

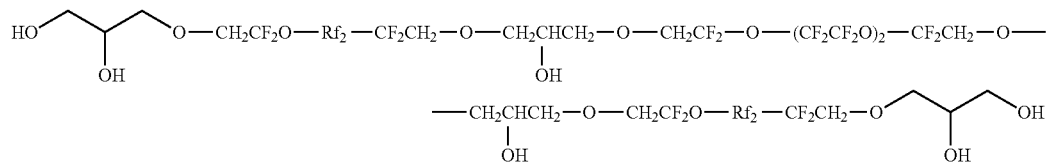

(AJ)

Comparative Example 11

A 300 mL round bottom flask was charged, under a nitrogen atmosphere, with the compound 2b represented by formula (M) (4 g) and t-butanol (40 mL), and stirring was performed until a uniform mixture was obtained. Next, epibromohydrin (2.9 mL) and potassium tert-butoxide (0.5 g) were added to the mixture, and the mixture was stirred for 9 hours while heating at 70° C., and was then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the residue was then separated by column chromatography. The above steps yielded a colorless and transparent liquid compound 6b (0.7 g) represented by a formula (AK). $Rf_2$ in the following formula (AK) is represented by the formula (RF-2) shown above.

$^1$H-NMR and $^{19}$F-NMR measurements of the obtained compound 6b were performed, and the structure was identified based on the following results.

(Identification Data)

$^1$H-NMR (acetone-$D_6$): δ [ppm]=2.59 (2H), 2.76 (2H), 3.11 (2H), 3.56 (2H), 3.71 to 4.02 (16H), 4.05 to 4.20 (8H)

$^{19}$F-NMR (acetone-$D_6$): δ [ppm]=−91.15 to −88.51 (48F), −78.81 to −78.45 (12F)

[Chemical formula 81]

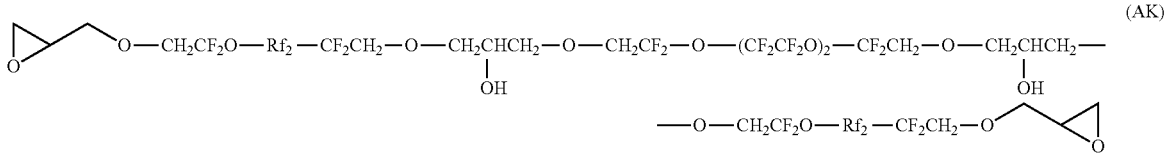

(AK)

A 300 mL round bottom flask was charged, under a nitrogen atmosphere, with the compound 6b represented by formula (AK) (1 g) and t-butanol (10 mL), and stirring was performed until a uniform mixture was obtained. Subsequently, ethylene glycol (2 mL) and potassium tert-butoxide (0.15 g) were added to the mixture, and the resulting mixture was stirred for 9 hours while heating at 70° C., and was then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the residue was then separated by column chromatography. The above steps yielded a colorless and transparent liquid compound AL; 8b (0.7 g) represented by a formula (AL). $Rf_2$ in the following formula (AL) is represented by the formula (RF-2) shown above.

$^1$H-NMR and $^{19}$F-NMR measurements of the obtained compound AL were performed, and the structure was identified based on the following results.

(Identification Data)

$^1$H-NMR (acetone-$D_6$): δ [ppm]=3.46 to 3.65 (8H), 3.65 to 3.81 (10H), 3.81 to 4.20 (22H)

$^{19}$F-NMR (acetone-$D_6$): δ [ppm]=−91.15 to −88.51 (48F), −78.81 to −78.45 (12F)

[Chemical formula 82]

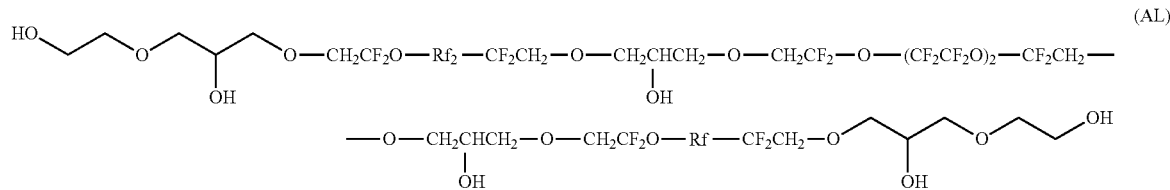
(AL)

Comparative Example 12

A 300 mL round bottom flask was charged, under a nitrogen atmosphere, with the compound 6b represented by formula (AK) (1 g) and t-butanol (10 mL), and stirring was performed until a uniform mixture was obtained. Subsequently, 2,2,3,3-fluorobutane-1,4-diol (5 g) and potassium tert-butoxide (0.1 g) were added to the mixture, and the resulting mixture was stirred for 9 hours while heating at 70° C., and was then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the residue was then separated by column chromatography. The above steps yielded a colorless and transparent liquid compound AM; 10b (0.9 g) represented by a formula (AM). $Rf_2$ in the following formula (AM) is represented by the formula (RF-2) shown above.

$^1$H-NMR and $^{19}$F-NMR measurements of the obtained compound AM were performed, and the structure was identified based on the following results.
(Identification Data)
$^1$H-NMR (acetone-$D_6$): δ [ppm]=3.65 to 4.07 (24H), 4.07 to 4.25 (16H)
$^{19}$F-NMR (acetone-$D_6$): δ [ppm]=−125.27 (4F), −123.31 (4F), −91.15 to −88.51 (48F), −78.81 to −78.45 (12F)

[Chemical formula 83]

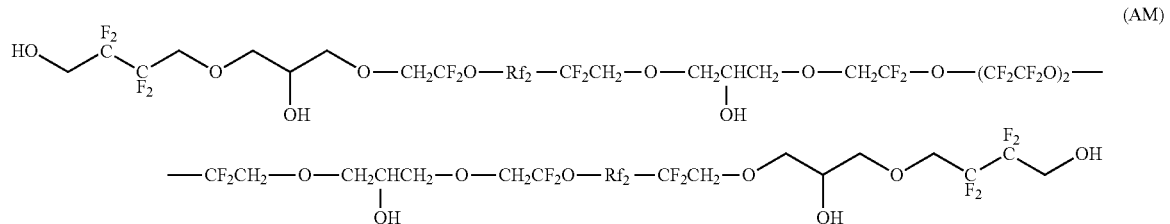
(AM)

Comparative Example 13

The compound T; 2c represented by formula (T) and synthesized in Example 10 was used.

Comparative Example 14

A 50 mL round bottom flask was charged, under a nitrogen atmosphere, with the compound 2c represented by formula (T) (4 g) and t-butanol (40 mL), and stirring was performed until a uniform mixture was obtained. Subsequently, potassium tert-butoxide (0.1 g) was added to the mixture, and with the mixture undergoing stirring at 70° C., glycidol (250 μL) was added, and the resulting mixture was then stirred for 8 hours, and then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the residue was then separated by column chromatography. The above steps yielded a colorless and transparent liquid compound AN; 4c (0.9 g) represented by a formula (AN). $Rf_1$ in the following formula (AN) is represented by the formula (RF-1) shown above.

$^1$H-NMR and $^{19}$F-NMR measurements of the obtained compound AN were performed, and the structure was identified based on the following results.
(Identification Data)
$^1$H-NMR (acetone-D$_6$): δ [ppm]=3.42 to 3.59 (2H), 3.61 to 3.83 (9H), 3.83 to 4.04 (9H), 4.04 to 4.28 (12H)
$^{19}$F-NMR (acetone-D$_6$): δ [ppm]=−91.15 to −88.51 (32F), −80.60 (4F), −78.81 to −78.45 (8F), −55.65 to −51.59 (12F)

[Chemical formula 84]

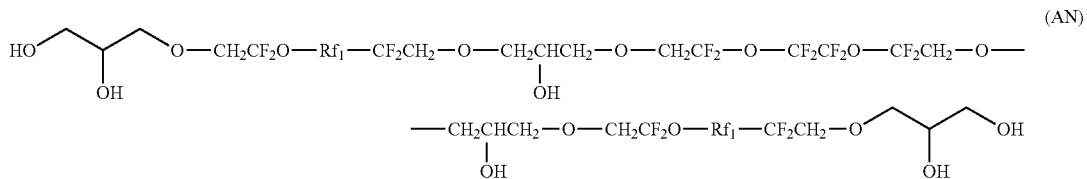

(AN)

Comparative Example 15

The compound W; 19a represented by formula (W) and synthesized in Example 11 was used.

Comparative Example 16

A 50 mL, round bottom flask was charged, under a nitrogen atmosphere, with the compound 19a represented by formula (W) (3.5 g) and t-butanol (40 mL), and stirring was performed until a uniform mixture was obtained. Subsequently, potassium tert-butoxide (0.1 g) was added to the mixture, and with the mixture undergoing stirring at 70° C., glycidol (250 μL) was added, and the resulting mixture was then stirred for 8 hours, and then cooled to 25° C.

Subsequently, a neutralization was performed by adding hydrochloric acid to the round bottom flask, water washing, collection, dewatering and filtering were then performed in the same manner as that described for the compound 2a represented by formula (13) in Example 1, and the residue was then separated by column chromatography. The above steps yielded a colorless and transparent liquid compound AO; 21a (0.9 g) represented by a formula (AO). Rf$_1$ in the following formula (AO) is represented by the formula (RF-1) shown above.

$^1$H-NMR and $^{19}$F-NMR measurements of the obtained compound AO were performed, and the structure was identified based on the following results.
(Identification Data)
$^1$H-NMR (acetone-D$_6$): δ [ppm]=3.41 to 3.81 (11H), 3.81 to 4.16 (21H)
$^{19}$F-NMR (acetone-D$_6$): δ [ppm]=−91.15 to −88.51 (42F), −80.61 (6F), −78.75 (6F), −55.65 to −51.59 (18F)

[Chemical formula 85]

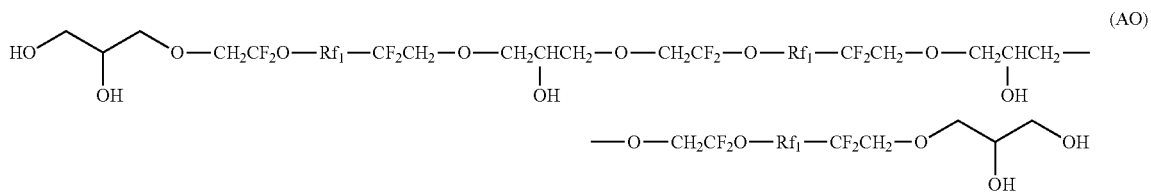

(AO)

Comparative Example 17

A 300 mL round bottom flask was charged, under a nitrogen atmosphere, with the compound 19a represented by formula (W) (4 g) and t-butanol (40 mL), and stirring was performed until a uniform mixture was obtained. Next, epibromohydrin (2.9 mL) and potassium tert-butoxide (0.1 g) were added to the mixture, and the mixture was stirred for 9 hours while heating at 70° C., and was then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the residue was then separated by column chromatography. The above steps yielded a colorless and transparent liquid compound 23a (0.8 g) represented by a formula (AP). $Rf_1$ in the following formula (AP) is represented by the formula (RE-1) shown above.

$^1$H-NMR and $^{19}$F-NMR measurements of the obtained compound 23a were performed, and the structure was identified based on the following results.

(Identification Data)

$^1$H-NMR (acetone-$D_6$): δ [ppm]=2.59 (2H), 2.76 (2H), 3.11 (2H), 3.41 to 3.81 (8H), 3.81 to 4.16 (18H)

$^{19}$F-NMR (acetone-$D_6$): δ [ppm]-91.15 to −88.51 (42F), −80.88 to −80.34 (6F), −78.93 to −78.30 (6F), −55.65 to −51.59 (18F)

[Chemical formula 86]

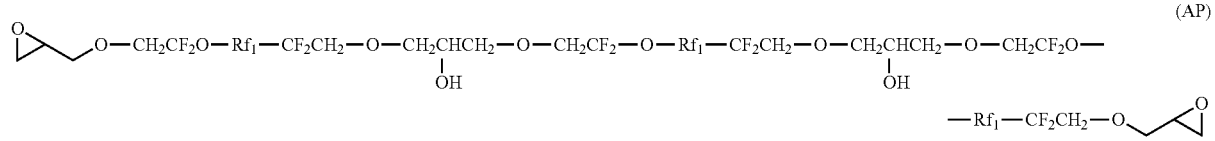

(AP)

A 300 mL round bottom flask was charged, under a nitrogen atmosphere, with the compound 23a represented by formula (AP) (1 g) and t-butanol (10 mL), and stirring was performed until a uniform mixture was obtained. Subsequently, ethylene glycol (2 mL) and potassium tert-butoxide (0.15 g) were added to the mixture, and the resulting mixture was stirred for 9 hours while heating at 70° C., and was then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the resulting residue was then separated by column chromatography. The above steps yielded a colorless and transparent liquid compound AQ; 25a (0.7 g) represented by a formula (AQ) shown below. $Rf_1$ in the following formula (AQ) is represented by the formula (RF-1) shown above.

$^1$H-NMR and $^{19}$F-NMR measurements of the obtained compound AQ were performed, and the structure was identified based on the following results.

(Identification Data)

$^1$H-NMR (acetone-$D_6$): δ [ppm]=3.46 to 3.63 (8H), 3.65 to 3.81 (10H), 3.81 to 4.18 (22H)

$^{19}$F-NMR (acetone-$D_6$): δ [ppm]=−91.15 to −88.51 (42F), −80.88 to −80.34 (6F), −78.93 to −78.30 (6F), −55.65 to −51.59 (I 8F)

[Chemical formula 87]

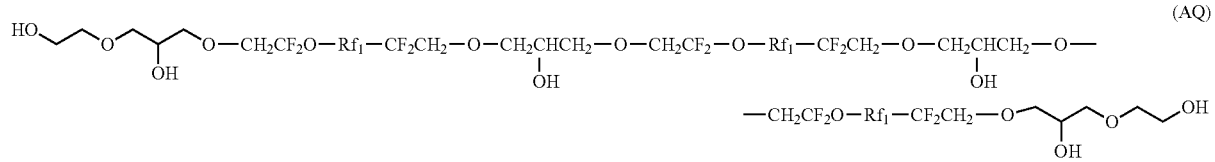

(AQ)

Comparative Example 18

Fomblin Z-tetraol manufactured by Solvay Solexis S.A. (molecular weight: about 2,000, shown below in formula (AR)) was used. This compound was termed compound AR.

[Chemical formula 88]

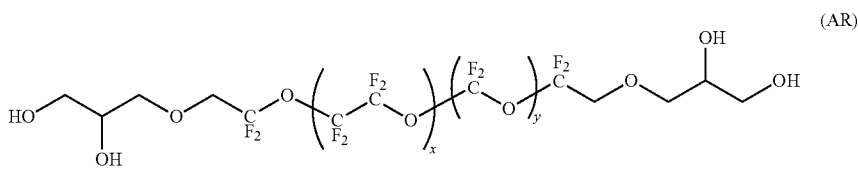

(AR)

(In formula (AR), x represents an integer of 1 to 7, and y represents an integer of 1 to 7.)

Comparative Examples 19 and 20

A 500 mL round bottom flask was charged, under a nitrogen atmosphere, with a fluoropolyether represented by $HOCH_2CF_2O(CF_2CF_2O)_m(CF_2O)_nCF_2CH_2OH$ (wherein m=1 to 7, n=1 to 7, number average molecular weight: 2,000, molecular weight distribution: 1.1) (10 g) and t-butanol (15 mL), and stirring was performed until a uniform mixture was obtained. Subsequently, potassium tert-butoxide (1.5 g) was added to the mixture, stirring was performed for one hour while heating at 70° C., epibromohydrin (8.0 g) was then added dropwise to the mixture, and the resulting mixture was stirred for 5 hours while heating at 70° C., and was then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the residue was then separated by column chromatography. The above steps yielded a colorless and transparent liquid compound 1 (3.0 g) represented by a formula (AS), and a colorless and transparent liquid compound 2 (1.0 g) represented by a formula (AT).

$^1$H-NMR and $^{19}$F-NMR measurements of the obtained compound 1 were performed, and the structure was identified based on the following results.
(Identification Data)
$^1$H-NMR (acetone-$D_6$): δ [ppm]=2.60 (1H), 2.77 (1H), 3.12 (1H), 3.57 (1H), 3.70 to 4.29 (5H)
$^{19}$F-NMR (acetone-$D_6$): S [ppm]=−91.15 to −88.51 (20F), −83.21 (1F), −81.22 (1F), −80.61 (1F), −78.75 (1F), −55.65 to −51.59 (10F)

[Chemical formula 89]

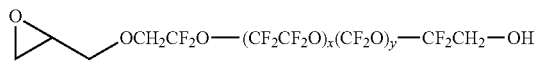

(AS)

(In formula (AS), x represents an integer of 1 to 7, and y represents an integer of 1 to 7.)
$^1$H-NMR and $^{19}$F-NMR measurements of the obtained compound 2 were performed, and the structure was identified based on the following results.
(Identification Data)
$^1$H-NMR (acetone-$D_6$): δ [ppm]=2.60 (2H), 2.77 (2H), 3.12 (2H), 3.57 (2H), 3.70 to 4.29 (6H)
$^{19}$F-NMR (acetone-$D_6$): δ [ppm]=−91.15 to −88.51 (20F), −80.61 (2F), −78.75 (2F), −55.65 to −51.59 (10F)

[Chemical formula 90]

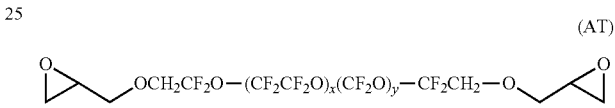

(AT)

(In formula (AT), x represents an integer of 1 to 7, and y represents an integer of 1 to 7.)

Comparative Example 19

A 300 mL round bottom flask was charged, under a nitrogen atmosphere, with the compound 1 represented by formula (AS) (1 g) and t-butanol (10 mL), and stirring was performed until a uniform mixture was obtained. Subsequently, ethylene glycol (1.5 mL) and potassium tert-butoxide (0.1 g) were added to the mixture, and the resulting mixture was stirred for 9 hours while heating at 70° C., and was then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the resulting residue was then separated by column chromatography. The above steps yielded a colorless and transparent liquid compound AU; 3 (0.7 g) represented by a formula (AU) shown below.

$^1$H-NMR and $^{19}$F-NMR measurements of the obtained compound AU were performed, and the structure was identified based on the following results.
(Identification Data)
$^1$H-NMR (acetone-$D_6$): δ [ppm]=3.30 to 4.50 (13H)
$^{19}$F-NMR (acetone-$D_6$): δ [ppm]=−91.15 to −88.51 (20F), −83.21 (1F), −81.22 (1F), −80.61 (1F), −78.75 (1F), −55.65 to −51.59 (10F)

[Chemical formula 91]

(AU)

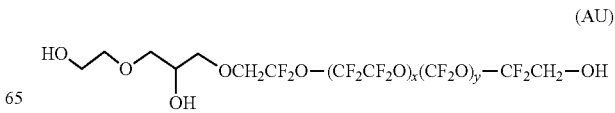

(In formula (AU), x represents an integer of 1 to 7, and y represents an integer of 1 to 7.)

Comparative Example 20

A 300 mL round bottom flask was charged, under a nitrogen atmosphere, with the compound 2 represented by formula (AT) (1 g) and t-butanol (10 mL), and stirring was performed until a uniform mixture was obtained. Subsequently, ethylene glycol (1.5 mL) and potassium tert-butoxide (0.15 g) were added to the mixture, and the resulting mixture was stirred for 9 hours while heating at 70° C., and was then cooled to 25° C.

Subsequently, a neutralization was performed by adding hydrochloric acid to the round bottom flask, water washing, collection, dewatering and filtering were then performed in the same manner as that described for the compound 2a represented by formula (B) in Example 1, and the resulting residue was then separated by column chromatography. The above steps yielded a colorless and transparent liquid compound AV; 4 (0.5 g) represented by a formula (AV) shown below.

$^1$H-NMR and $^{19}$F-NMR measurements of the obtained compound AV were performed, and the structure was identified based on the following results.
(Identification Data)
$^1$H-NMR (acetone-$D_6$): δ [ppm]=3.30 to 4.50 (22H)
$^{19}$F-NMR (acetone-$D_6$): δ [ppm]=−91.15 to −88.51 (20F), −80.61 (2F), −78.75 (2F), −55.65 to −51.59 (10F)

[Chemical formula 92]

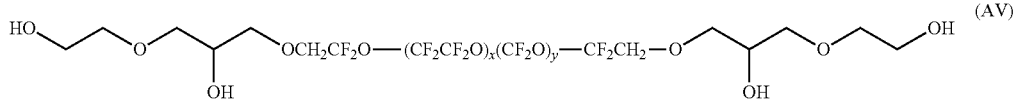

(In formula (AV), x represents an integer of 1 to 7, and y represents an integer of 1 to 7.)

The structures of $R^1$ to $R^5$ in formula (1) for the compounds of Examples 1 to 12 and Comparative Examples 1 to 20 obtained in the manner described above are summarized in Table 1 and Table 2.

In Table 1 and Table 2, $Rf_1$ is represented by the above formula (RF-1), and $Rf_2$ is represented by the above formula (RF-2).

TABLE 1

| | | Terminals | | PFPE | | |
|---|---|---|---|---|---|---|
| | Compound | R5 | R4 | R1 | R3 | R2 |
| Example 1 | D | hydroxyl group | formula (2-1) r = 0 | formula (3) n = 0, m = 2 | $CF_2ORf_1CF_2$ | formula (6) w = 1 |
| Example 2 | O | hydroxyl group | formula (2-2) p = 1 | formula (3) n = 0, m = 2 | $CF_2ORf_1CF_2$ | formula (6) w = 1 |
| Example 3 | H | hydroxyl group | formula (2-3) s = 2 | formula (3) n = 0, m = 2 | $CF_2ORf_1CF_2$ | formula (6) w = 1 |
| Example 4 | J | hydroxyl group | formula (2-4) t = 1 | formula (3) n = 0, m = 2 | $CF_2ORf_1CF_2$ | formula (6) w = 1 |
| Example 5 | K | hydroxyl group | formula (2-5) q = 2 | formula (3) n = 0, m = 2 | $CF_2ORf_1CF_2$ | formula (6) w = 1 |
| Example 6 | L | hydroxyl group | formula (2-5) q = 3 | formula (3) n = 0, m = 2 | $CF_2ORf_1CF_2$ | formula (6) w = 1 |
| Example 7 | O | hydroxyl group | formula (2-1) r = 0 | formula (3) n = 0, m = 2 | $CF_2ORf_2CF_2$ | formula (6) w = 1 |
| Example 8 | Q | hydroxyl group | formula (2-2) p = 1 | formula (3) n = 0, m = 2 | $CF_2ORf_2CF_2$ | formula (6) w = 1 |
| Example 9 | R | hydroxyl group | formula (2-3) s = 2 | formula (3) n = 0, m = 2 | $CF_2ORf_2CF_2$ | formula (6) w = 1 |
| Example 10 | U | hydroxyl group | formula (2-1) r = 0 | formula (3) n = 0, m = 1 | $CF_2ORf_1CF_2$ | formula (6) w = 1 |
| Example 11 | X | hydroxyl group | formula (2-1) r = 0 | $CF_2ORf_1CF_2$ | $CF_2ORf_1CF_2$ | formula (6) w = 1 |
| Example 12 | Z | hydroxyl group | formula (2-2) p = 1 | $CF_2ORf_1CF_2$ | $CF_2ORf_1CF_2$ | formula (6) w = 1 |

$Rf_1$ is a group represented by formula (RF-1), wherein x represents an integer of 1 to 7, and y represents an integer of 1 to 7.
$Rf_2$ is a group represented by formula (RF-2), wherein z represents an integer of 1 to 9.

TABLE 2

| | | Terminals | | PFPE | | |
|---|---|---|---|---|---|---|
| | Compound | R5 | R4 | R1 | R3 | R2 |
| Comparative Example 1 | B | hydroxyl group | hydroxyl group | formula (3) n = 0, m = 2 | $CF_2ORf_1CF_2$ | formula (6) w = 1 |
| Comparative Example 2 | AA | formula (2-1) r = 0 | formula (2-1) r = 0 | formula (3) n = 0, m = 2 | $CF_2ORf_1CF_2$ | formula (6) w = 1 |
| Comparative Example 3 | AC | formula (2-2) p = 1 | formula (2-2) p = 1 | formula (3) n = 0, m = 2 | $CF_2ORf_1CF_2$ | formula (6) w = 1 |
| Comparative Example 4 | AD | formula (2-3) s = 2 | formula (2-3) s = 2 | formula (3) n = 0, m = 2 | $CF_2ORf_1CF_2$ | formula (6) w = 1 |
| Comparative Example 5 | AE | formula (2-4) t = 1 | formula (2-4) t = 1 | formula (3) n = 0, m = 2 | $CF_2ORf_1CF_2$ | formula (6) w = 1 |
| Comparative Example 6 | AF | formula (2-5) q = 2 | formula (2-5) q = 2 | formula (3) n = 0, m = 2 | $CF_2ORf_1CF_2$ | formula (6) w = 1 |
| Comparative Example 7 | AG | formula (2-5) q = 3 | formula (2-5) q = 3 | formula (3) n = 0, m = 2 | $CF_2ORf_1CF_2$ | formula (6) w = 1 |
| Comparative Example 8 | M | hydroxyl group | hydroxyl group | formula (3) n = 0, m = 2 | $CF_2ORf_2CF_2$ | formula (6) w = 1 |
| Comparative Example 9 | AH | hydroxyl group | hydroxyl group | formula (3) n = 0, m = 2 | formula (3) n = 0, m = 2 | formula (6) w = 1 |
| Comparative Example 10 | AJ | formula (2-1) r = 0 | formula (2-1) r = 0 | formula (3) n = 0, m = 2 | $CF_2ORf_2CF_2$ | formula (6) w = 1 |
| Comparative Example 11 | AL | formula (2-2) p = 1 | formula (2-2) p = 1 | formula (3) n = 0, m = 2 | $CF_2ORf_2CF_2$ | formula (6) w = 1 |
| Comparative Example 12 | AM | formula (2-3) s = 2 | formula (2-3) s = 2 | formula (3) n = 0. m = 2 | $CF_2ORf_2CF_2$ | formula (6) w = 1 |
| Comparative Example 13 | T | hydroxyl group | hydroxyl group | formula (3) l = 0, m = 1 | $CF_2ORf_1CF_2$ | formula (6) w = 1 |
| Comparative Example 14 | AN | formula (2-1) r = 0 | formula (2-1) r = 0 | formula (3) n = 0, m = 1 | $CF_2ORf_1CF_2$ | formula (6) w = 1 |
| Comparative Example 15 | W | hydroxyl group | hydroxyl group | $CF_2ORf_1CF_2$ | $CF_2ORf_1CF_2$ | formula (6) w = 1 |
| Comparative Example 16 | AO | formula (2-1) r = 0 | formula (2-1) r = 0 | $CF_2ORf_1CF_2$ | $CF_2ORf_1CF_2$ | formula (6) w = 1 |
| Comparative Example 17 | AQ | formula (2-2) p = 1 | formula (2-2) p = 1 | $CF_2ORf_1CF_2$ | $CF_2ORf_1CF_2$ | formula (6) w = 1 |
| Comparative Example 18 | AR | formula (2-1) r = 0 | formula (2-1) r = 0 | formula (3) | — | — |
| Comparative Example 19 | AU | hydroxyl group | formula (2-2) p = 1 | formula (3) n = 1 to 7, m = 1 to 7 | — | — |
| Comparative Example 20 | AV | formula (2-2) p = 1 | formula (2-2) p = 1 | formula (3) n = 1 to 7, m = 1 to 7 | — | — |

$Rf_1$ is a group represented by formula (RF-1), wherein x represents an integer of 1 to 7, and y represents an integer of 1 to 7.
$Rf_2$ is a group represented by formula (RF-2), wherein z represents an integer of 1 to 9.

The number average molecular weights of the compounds of Examples 1 to 12 and Comparative Examples 1 to 20 obtained in the manner described above were determined from the $^{19}$F-NMR measurements described above. The results are shown in Table 3 and Table 4.

Further, using the compounds obtained in Examples 1 to 12 and Comparative Examples 1 to 20, evaluations were conducted by using the methods described below to perform a silicone contamination resistance test, a measurement of the adhesion (bonding rate) between the lubricant layer and the protective layer, and a measurement of head contamination. The results are shown in Table 3 and Table 4.

(Silicone Contamination Resistance Test)

The compound was dissolved in Vertrel (a registered trademark) XF (a product name, manufactured by Mitsui DuPont Fluorochemicals Co., Ltd.), and a dilute solution of the compound was prepared so that the film thickness upon application of the solution was 10 Å to 12 Å. The thus obtained dilute solution was applied by a dipping method to the protective layer of a magnetic recording medium of diameter 65 mm having the structure illustrated in FIG. 1, thus forming a lubricant layer. Application of the dilute solution was performed under conditions including a clipping speed of 10 mm/sec, dipping time of 30 sec, and a withdrawal speed of 1.2 mm/sec.

The thickness of the obtained lubricant layer was measured using an FT-JR (product name: Nicolet iS50, manufactured by Thermo Fisher Scientific Inc.). The result is shown in Table 3 or Table 4.

Figure 2:
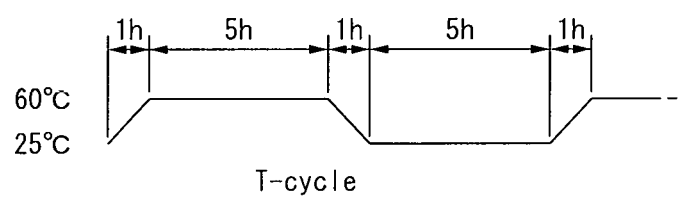
FIG. 2 is a diagram describing the environment for performing repetition of continuous LUL operations.

Subsequently, an LUL (Load/Unload) hard disk drive was prepared, and the magnetic recording medium with the lubricant layer formed thereon was mounted in the hard disk drive. A perpendicular magnetic recording head was used for the hard disk drive head. A commercially available silicone rubber gel chip (1 cm×1 cm×0.5 cm) was placed inside the hard disk drive, and continuous LUL operations were repeated under the conditions described below until the drive current of the spindle motor exceeded a threshold. As shown in FIG. 2, the conditions for the continuous LUL operations involved a 5-hour operating cycle at 25° C.→60° C.→25° C. (with one hour for each of startup and shutdown) under a dry atmosphere (relative humidity of not more than 10%). The time from the start of continuous LUL operations until the point where the drive current of the spindle motor exceeded the threshold was deemed the endurance time.

Provided the compound in the lubricant layer is disposed uniformly across the protective layer with no voids, adhesion of cyclic siloxanes generated by vaporization from the silicone rubber gel chip to the magnetic recording medium can be prevented. Accordingly, no extra load is placed on the spindle motor of the hard disk drive, and the endurance time lengthens. In contrast, if the compound in the lubricant layer has aggregated, forming voids in the lubricant layer, then the vaporized cyclic siloxanes can adhere to the magnetic recording medium. This results in extra load being placed on the hard disk drive spindle motor, leading to a shortening of the endurance time.

Silicone Contamination Resistance Test Evaluation
  o: endurance time of 150 hours or longer
  Δ: endurance time of at least 100 hours but less than 150 hours
  x: endurance time of less than 100 hours
(Measurement of Adhesion (Bonding Rate) Between Lubricant Layer and Protective Layer)

A lubricant layer was formed on the protective layer of a magnetic recording medium in the same manner as that described above for the silicone contamination durability test, and the thickness of the lubricant layer was measured in the same manner as that described for the silicone contamination durability test.

Subsequently, the magnetic recording medium with the lubricant layer formed thereon was washed by dipping the magnetic recording medium in the solvent Vertrel for 10 minutes and then pulling the magnetic recording medium from the solvent. The speed with which the magnetic recording medium was dipped in the solvent was 10 mm/sec, and the withdrawal speed was 1.2 mm/sec.

Subsequently, the thickness of the lubricant layer was remeasured using the same method as the lubricant layer thickness measurement performed prior to washing.

The thickness of the lubricant layer prior to washing was termed A, the thickness of the lubricant layer after washing (after clipping in the solvent) was termed B, and the bonding rate of the lubricant layer was calculated from the ratio between A and B ((B/A)×100(%)). Using this calculated bonding rate, the adhesion between the lubricant layer and the protective layer was evaluated against the criteria shown below.

Evaluation of Adhesion (Bonding Rate)
  o: bonding rate of at least 50%
  x: bonding rate of less than 50%
(Measurement of Head Contamination)

A lubricant layer was formed on the protective layer of a magnetic recording medium in the same manner as that described above for the silicone contamination durability test. The magnetic recording medium with the lubricant layer formed thereon was then mounted in an LUL (Load/Unload) hard disk drive in the same manner as that described above for the silicone contamination durability test. A perpendicular magnetic recording head was used for the hard disk drive head. The hard disk drive was operated for 10 minutes, and the head portion was then removed from the hard disk drive.

The surface of the head portion was inspected using an optical microscope within 5 minutes of stopping the hard disk drive operation. The region in the vicinity of the pole chip (the magnetic recording and playback element of the head) was observed at a magnification of 1,000× with a field of view of 100 μm×100 μm, and the level of contamination was evaluated against the following criteria.

Evaluation of Head Contamination
  o: no liquid droplet-like or clay-like foreign substances (smears) were observed within the field of view
  x: liquid droplet-like or clay-like foreign substances (smears) were observed within the field of view

TABLE 3

| | Number average molecular weight | Film thickness Å | Silicone contamination durability | | Bonding rate | | Head contamination | Overall evaluation |
|---|---|---|---|---|---|---|---|---|
| | | | Time hr | Result | % | Result | | |
| Example 1 | 2184 | 11 | 591 | o | 62 | o | o | o |
| Example 2 | 2228 | 10 | 622 | o | 75 | o | o | o |
| Example 3 | 2328 | 10 | 488 | o | 74 | o | o | o |
| Example 4 | 2198 | 10 | 599 | o | 74 | o | o | o |
| Example 5 | 2242 | 10 | 587 | o | 73 | o | o | o |
| Example 6 | 2256 | 10 | 552 | o | 73 | o | o | o |
| Example 7 | 2288 | 10 | 455 | o | 61 | o | o | o |
| Example 8 | 2332 | 10 | 536 | o | 75 | o | o | o |
| Example 9 | 2432 | 10 | 502 | o | 77 | o | o | o |
| Example 10 | 2068 | 11 | 580 | o | 63 | o | o | o |
| Example 11 | 2584 | 10 | 453 | o | 65 | o | o | o |
| Example 12 | 2628 | 11 | 577 | o | 74 | o | o | o |

TABLE 4

| | Number average molecular weight | Film thickness Å | Silicone contamination durability Time hr | Result | Bonding rate % | Result | Head contamination | Overall evaluation |
|---|---|---|---|---|---|---|---|---|
| Comparative Example 1 | 2109 | 10 | 276 | ○ | 42 | X | ○ | X |
| Comparative Example 2 | 2259 | 11 | 647 | ○ | 75 | ○ | X | X |
| Comparative Example 3 | 2347 | 10 | 598 | ○ | 78 | ○ | X | X |
| Comparative Example 4 | 2547 | 10 | 606 | ○ | 79 | ○ | X | X |
| Comparative Example 5 | 2287 | 10 | 612 | ○ | 75 | ○ | X | X |
| Comparative Example 6 | 2375 | 11 | 557 | ○ | 76 | ○ | X | X |
| Comparative Example 7 | 2403 | 10 | 516 | ○ | 77 | ○ | X | X |
| Comparative Example 8 | 2213 | 10 | 263 | ○ | 43 | X | ○ | X |
| Comparative Example 9 | 1327 | 11 | 278 | ○ | 38 | X | ○ | X |
| Comparative Example 10 | 2363 | 12 | 513 | ○ | 75 | ○ | X | X |
| Comparative Example 11 | 2451 | 11 | 485 | ○ | 73 | ○ | X | X |
| Comparative Example 12 | 2651 | 10 | 435 | ○ | 75 | ○ | X | X |
| Comparative Example 13 | 1993 | 11 | 288 | ○ | 41 | X | ○ | X |
| Comparative Example 14 | 2143 | 12 | 621 | ○ | 68 | ○ | X | X |
| Comparative Example 5 | 2509 | 10 | 342 | ○ | 45 | X | ○ | X |
| Comparative Example 16 | 2659 | 11 | 523 | ○ | 73 | ○ | X | X |
| Comparative Example 17 | 2747 | 11 | 573 | ○ | 77 | ○ | X | X |
| Comparative Example 18 | 2000 | 11 | 48 | X | 45 | X | ○ | X |
| Comparative Example 19 | 2019 | 10 | 60 | X | 48 | X | ○ | X |
| Comparative Example 20 | 2123 | 10 | 44 | X | 32 | X | ○ | X |

As shown in Table 3, in each of Examples 1 to 12, the result for the silicone contamination test, and the evaluations of the adhesion (bonding rate) between the lubricant layer and the protective layer, and the head contamination were all a. Based on these results, it was evident that by forming a lubricant layer containing any of the compounds of Examples 1 to 12 on the protective layer of a magnetic recording medium, a lubricant layer could be obtained which, even when having a reduced thickness of 10 Å to 12 Å, was able to cover the surface of the protective layer with a high coverage rate, had excellent adhesion to the protective layer, and was unlikely to produce foreign matter (smears).

In contrast, as shown in Table 2 and Table 4, in Comparative Examples 1, 8, 9, 13 and 15, in which $R^4$ and $R^5$ were both hydroxyl groups, the adhesion between the lubricant layer and the protective layer was unsatisfactory.

Further, in each of Comparative Examples 2 to 7, 10 to 12, 14, 16 and 17, in which $R^4$ and $R^5$ were terminal groups represented by one of formulas (2-1) to (2-5), and $R^4$ and $R^5$ were the same, because the total number of hydroxyl groups contained in $R^4$ and $R^5$ was four, the evaluation for the bonding rate was a, but the head contamination evaluation was x.

Further, in each of Comparative Examples 18 to 20, which lacked $R^2$ and $R^3$, because the coverage rate was insufficient, the silicone contamination durability test evaluation was x. Further, in each of Comparative Examples 18 and 20, even though the total number of hydroxyl groups contained in $R^4$ and $R^5$ was four, because there were no $R^2$ groups, the bonding rate evaluation was x.

INDUSTRIAL APPLICABILITY

By using the lubricant for a magnetic recording medium according to the present invention, a lubricant layer can be obtained which, even when having reduced thickness, can cover the surface of the protective layer of a magnetic recording medium with a high coverage rate, has excellent adhesion to the protective layer, and is unlikely to produce foreign matter (smears).

DESCRIPTION OF THE REFERENCE SIGNS

10: Magnetic recording medium
11: Substrate
12: Adhesive layer

13: Soft magnetic layer
14: First base layer
15: Second base layer
16: Magnetic layer
17: Protective layer
18: Lubricant layer

The invention claimed is:

1. A fluorine-containing ether compound represented by a formula (1) shown below:

$$R^4-CH_2-R^3-CH_2-R^2-CH_2-R^1-CH_2-R^2-CH_2-R^3-CH_2-R^5 \quad (1)$$

wherein $R^1$ and $R^3$ represent identical or different perfluoropolyether chains, $R^2$ represents a linking group containing at least one polar group, one or both of $R^4$ and $R^5$ represent a terminal group containing two or more polar groups, $R^4$ and $R^5$ are different, and $R^4$ and $R^5$ are each a hydroxyl group or one terminal group selected from among formulas (2-1) to (2-5) shown below:

$$-O-\underset{H_2}{C}-\underset{OH}{\overset{H}{C}}-\underset{H_2}{C}-\left(O-\underset{H_2}{C}-\underset{OH}{\overset{H}{C}}-\underset{H_2}{C}\right)_r-OH \quad (2\text{-}1)$$

wherein r represents an integer of 0 to 4, $$-O-\underset{H_2}{C}-\underset{OH}{\overset{H}{C}}-\underset{H_2}{C}-\left(O-\underset{H_2}{C}-\underset{H_2}{C}\right)_p-OH \quad (2\text{-}2)$$

wherein p represents an integer of 1 to 5, $$-O-\underset{H_2}{C}-\underset{OH}{\overset{H}{C}}-\underset{H_2}{C}-O-\underset{H_2}{C}-\left(\underset{F_2}{C}\right)_s-\underset{H_2}{C}-OH \quad (2\text{-}3)$$

wherein s represents an integer of 2 to 5, $$-O-\underset{H_2}{C}-\underset{OH}{\overset{H}{C}}-\underset{H_2}{C}-\left(\underset{H_2}{C}\right)_t-OH \quad (2\text{-}4)$$

wherein t represents an integer of 1 to 5, $$-O-\underset{H_2}{C}-\underset{OH}{\overset{H}{C}}-\underset{H_2}{C}-O-\underset{H_2}{C}-\left(\underset{H_2}{C}\right)_q-OH \quad (2\text{-}5)$$

wherein q represents an integer of 2 to 5.

2. The fluorine-containing ether compound according to claim 1, wherein one or both of $R^1$ and $R^3$ in the formula (1) are represented by a formula (3) shown below:

$$-\underset{F_2}{C}-O-\left(\underset{F_2}{\overset{F_2}{C}}-\underset{F_2}{C}-O\right)_m-\left(\underset{F_2}{C}-O\right)_n-\underset{F_2}{C}- \quad (3)$$

wherein m represents an integer of 1 to 20, and n represents an integer of 0 to 10.

3. The fluorine-containing ether compound according to claim 1, wherein $R^3$ in the formula (1) is represented by a formula (4) shown below or a formula (5) shown below:

$$-\underset{F}{\overset{CF_3}{C}}-\left(O-\underset{F}{\overset{CF_3}{C}}-\underset{F_2}{C}\right)_u-O-\underset{F}{\overset{CF_3}{C}}- \quad (4)$$

wherein u represents an integer of 1 to 30, $$-\underset{F_2}{C}-\underset{F_2}{C}-\left(O-\underset{F_2}{C}-\underset{F_2}{C}-\underset{F_2}{C}\right)_v-O-\underset{F_2}{C}-\underset{F_2}{C}- \quad (5)$$

wherein v represents an integer of 1 to 30.

4. The fluorine-containing ether compound according to claim 1, wherein a number of carbon atoms in $R^2$ in the formula (1) is from 1 to 20.

5. The fluorine-containing ether compound according to claim 1, wherein $R^2$ in the formula (1) is represented by a formula (6) shown below:

$$\left(O-\underset{H_2}{C}-\underset{OH}{\overset{H}{C}}-\underset{H_2}{C}\right)_w-O- \quad (6)$$

wherein w represents an integer of 1 to 4.

6. The fluorine-containing ether compound according to claim 1, wherein the compound represented by the formula (1) is represented by a formula (D) shown below, and $Rf_1$ in the formula (D) is represented by a formula (RF-1) shown below:

$$HO-CH_2CF_2O-Rf_1-CF_2CH_2-O-CH_2\underset{OH}{CH}CH_2-O-CH_2CF_2-O-(CF_2CF_2O)_2-CF_2CH_2-O-CH_2\underset{OH}{CH}CH_2-O-CH_2CF_2O-Rf_1- \quad (D)$$

—CF$_2$CH$_2$—O—CH$_2$CH(OH)CH$_2$OH (RF-1)

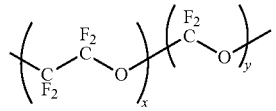

wherein x represents an integer of 1 to 7, and y represents an integer of 1 to 7.

7. The fluorine-containing ether compound according to claim 1, wherein the compound represented by the formula (1) is represented by a formula (G) shown below, and Rf$_1$ in the formula (G) is represented by a formula (RF-1):

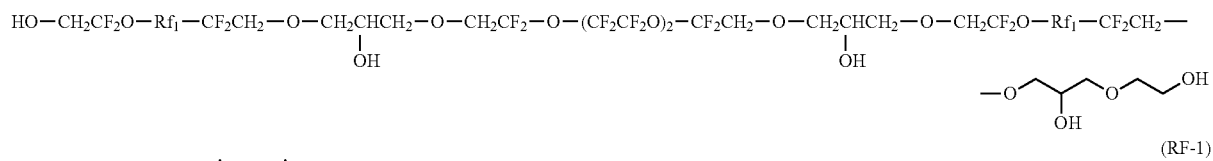

(G)

HO—CH$_2$CF$_2$O—Rf$_1$—CF$_2$CH$_2$—O—CH$_2$CHCH$_2$—O—CH$_2$CF$_2$—O—(CF$_2$CF$_2$O)$_2$—CF$_2$CH$_2$—O—CH$_2$CHCH$_2$—O—CH$_2$CF$_2$O—Rf$_1$—CF$_2$CH$_2$—
  |  OH
                                                                                                                                                          |  OH

—O—CH$_2$CH(OH)CH$_2$—O—CH$_2$CH$_2$OH (RF-1)

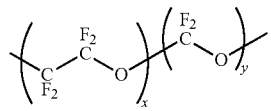

wherein x represents an integer of 1 to 7, and y represents an integer of 1 to 7.

8. The fluorine-containing ether compound according to claim 1, wherein the compound represented by the formula (1) is represented by a formula (H) shown below, and Rf$_1$ in the formula (H) is represented by a formula (RF-1):

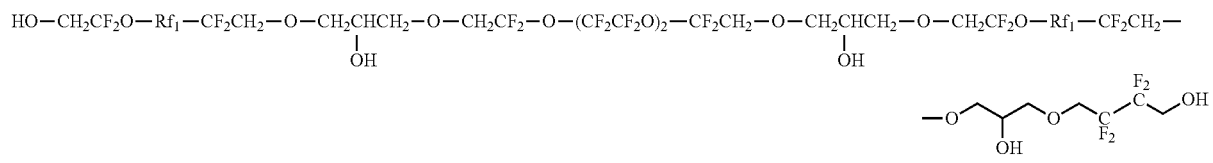

(H)

HO—CH$_2$CF$_2$O—Rf$_1$—CF$_2$CH$_2$—O—CH$_2$CHCH$_2$—O—CH$_2$CF$_2$—O—(CF$_2$CF$_2$O)$_2$—CF$_2$CH$_2$—O—CH$_2$CHCH$_2$—O—CH$_2$CF$_2$O—Rf$_1$—CF$_2$CH$_2$—
  |  OH
                                                                                                                                                          |  OH

—O—CH$_2$CH(OH)CH$_2$—O—CF$_2$CF$_2$CH$_2$OH (RF-1)

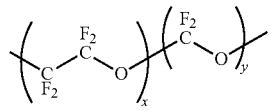

wherein x represents an integer of 1 to 7, and y represents an integer of 1 to 7.

9. The fluorine-containing ether compound according to claim 1, wherein the compound represented by the formula (1) is represented by a formula (J) shown below, and Rf$_1$ in the formula (J) is represented by a formula (RF-1):

(J)

HO—CH$_2$CF$_2$O—Rf$_1$—CF$_2$CH$_2$—O—CH$_2$CHCH$_2$—O—CH$_2$CF$_2$—O—(CF$_2$CF$_2$O)$_2$—CF$_2$CH$_2$—O—CH$_2$CHCH$_2$—O—CH$_2$CF$_2$O—Rf$_1$—CF$_2$CH$_2$—
  |  OH
                                                                                                                                                          |  OH

—O—CH$_2$CH(OH)CH$_2$CH$_2$OH

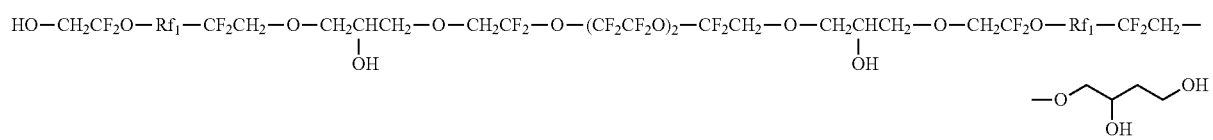

-continued

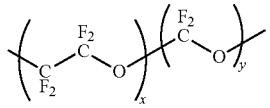
(RF-1)

wherein x represents an integer of 1 to 7, and y represents an integer of 1 to 7.

10. The fluorine-containing ether compound according to claim 1, wherein the compound represented by the formula (1) is represented by a formula (K) shown below, and $Rf_1$ in the formula (K) is represented by a formula (RF-1):

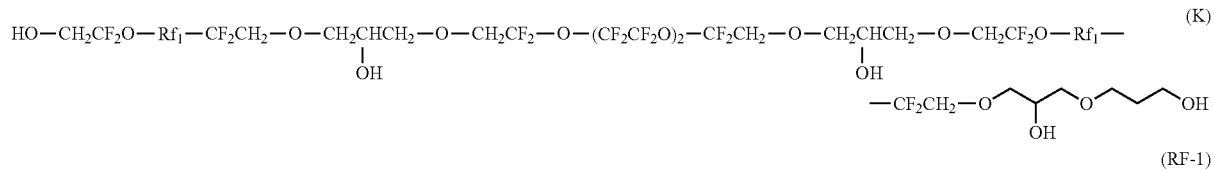
(K)

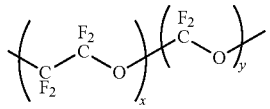
(RF-1)

wherein x represents an integer of 1 to 7, and y represents an integer of 1 to 7.

11. The fluorine-containing ether compound according to claim 1, wherein the compound represented by the formula (1) is represented by a formula (L) shown below, and $Rf_1$ in the formula (L) is represented by a formula (RF-1):

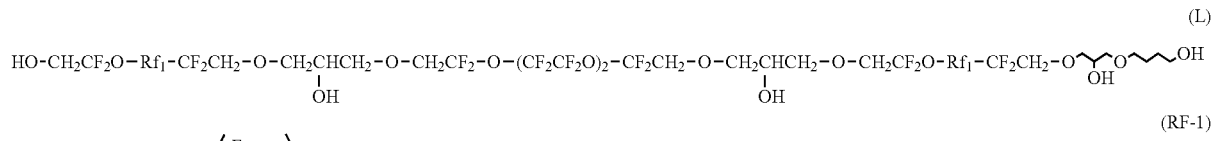
(L)

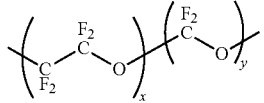
(RF-1)

wherein x represents an integer of 1 to 7, and y represents an integer of 1 to 7.

12. The fluorine-containing ether compound according to claim 1, wherein the compound represented by the formula (1) is represented by a formula (O) shown below, and $Rf_2$ in the formula (O) is represented by a formula (RF-2) shown below:

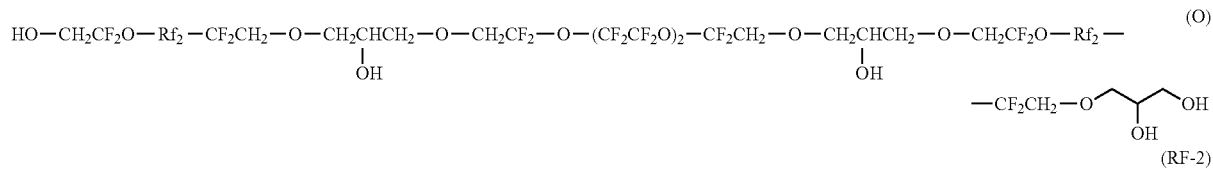
(O)

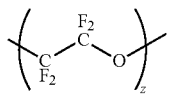
(RF-2)

wherein z represents an integer of 1 to 9.

13. The fluorine-containing ether compound according to claim 1, wherein the compound represented by the formula (1) is represented by a formula (Q) shown below, and Rf$_2$ in the formula (Q) is represented by a formula (RF-2):

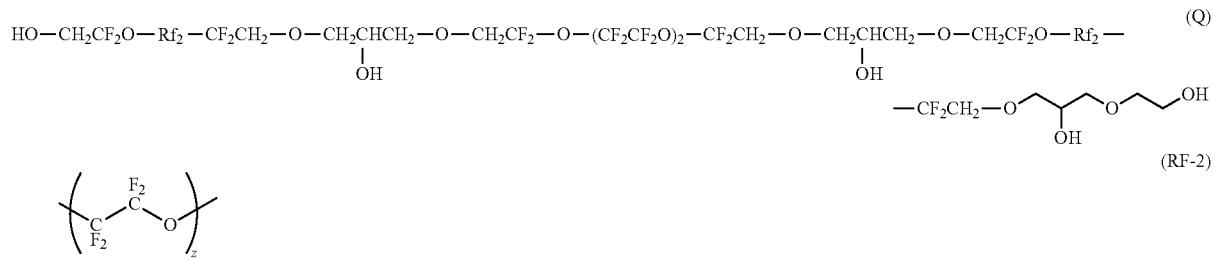
(Q)

(RF-2)

(RF-2)

wherein z represents an integer of 1 to 9.

14. The fluorine-containing ether compound according to claim 1, wherein the compound represented by the formula (1) is represented by a formula (R) shown below, and Rf$_2$ in the formula (R) is represented by a formula (RF-2):

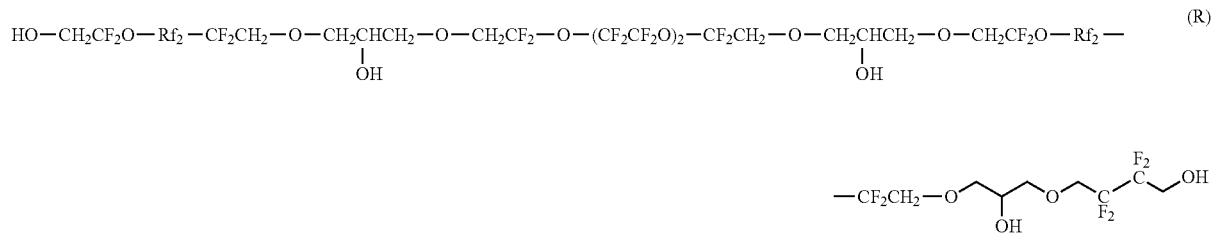
(R)

(RF-2)

(RF-2)

wherein z represents an integer of 1 to 9.

15. The fluorine-containing ether compound according to claim 1, wherein the compound represented by the formula (1) is represented by a formula (U) shown below, and Rf$_1$ in the formula (U) is represented by a formula (RF-1):

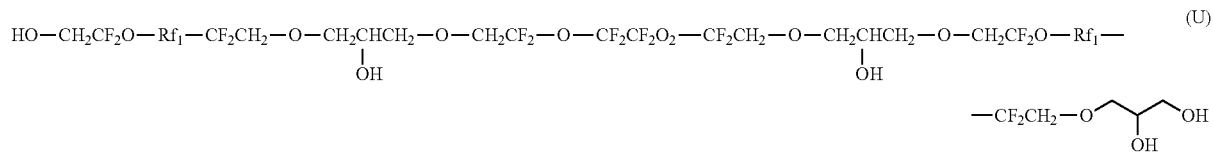
(U)

(RF-1)

(RF-1)

wherein x represents an integer of 1 to 7, and y represents an integer of 1 to 7.

16. The fluorine-containing ether compound according to claim 1, wherein the compound represented by the formula (1) is represented by a formula (X) shown below, and $Rf_1$ in the formula (X) is represented by a formula (RF-1):

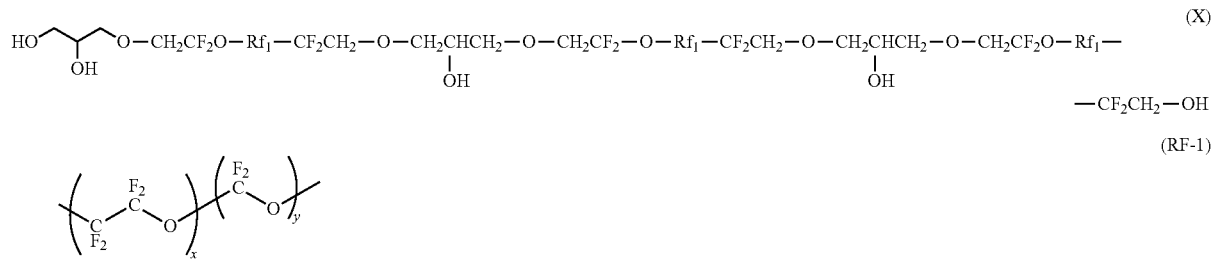

wherein x represents an integer of 1 to 7, and y represents an integer of 1 to 7.

17. The fluorine-containing ether compound according to claim 1, wherein the compound represented by the formula (1) is represented by a formula (Z) shown below, and $Rf_1$ in the formula (Z) is represented by a formula (RF-1):

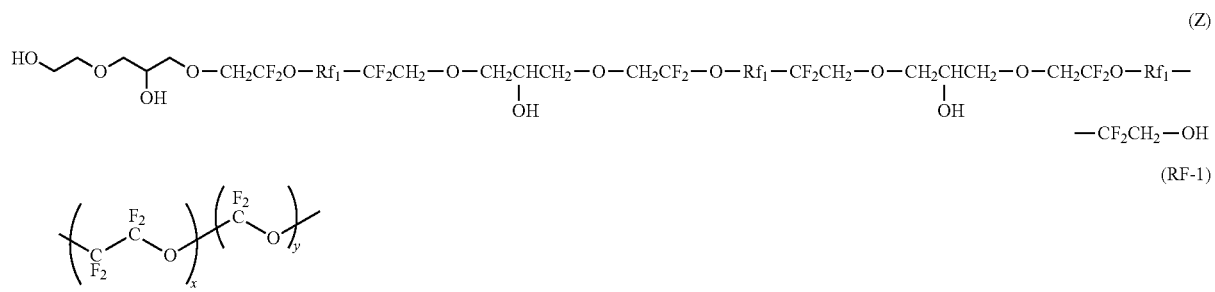

wherein x represents an integer of 1 to 7, and y represents an integer of 1 to 7.

18. The fluorine-containing ether compound according to claim 1, having a number average molecular weight within a range from 1,000 to 10,000.

19. A lubricant for a magnetic recording medium comprising the fluorine-containing ether compound according to claim 1.

20. A magnetic recording medium comprising at least a magnetic layer, a protective layer and a lubricant layer provided sequentially on a substrate, wherein the lubricant layer contains the fluorine-containing ether compound according to claim 1.

21. The magnetic recording medium according to claim 20, wherein an average thickness of the lubricant layer is from 0.5 nm to 3 nm.

22. A fluorine-containing ether compound represented by a formula (1) shown below:

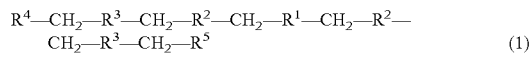

wherein $R^1$ and $R^3$ represent identical or different perfluoropolyether chains, $R^2$ represents a linking group containing at least one polar group, one of $R^4$ and $R^5$ represents a terminal group containing two or more polar groups, and the other of $R^4$ and $R^5$ is a hydroxyl group.

23. A lubricant for a magnetic recording medium comprising the fluorine-containing ether compound according to claim 22.

24. A magnetic recording medium comprising at least a magnetic layer, a protective layer and a lubricant layer provided sequentially on a substrate, wherein the lubricant layer contains the fluorine-containing ether compound according to claim 22.

* * * * *